United States Patent
Tsukagoshi

(10) Patent No.: US 9,314,224 B2
(45) Date of Patent: Apr. 19, 2016

(54) IMAGE PROCESSING SYSTEM, IMAGE PROCESSING APPARATUS, AND IMAGE PROCESSING METHOD

(75) Inventor: Shinsuke Tsukagoshi, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 676 days.

(21) Appl. No.: 13/544,319

(22) Filed: Jul. 9, 2012

(65) Prior Publication Data

US 2013/0021331 A1    Jan. 24, 2013

(30) Foreign Application Priority Data

Jul. 19, 2011  (JP) ................................. 2011-158254

(51) Int. Cl.

| G06T 15/00 | (2011.01) |
|---|---|
| A61B 8/00 | (2006.01) |
| A61B 6/02 | (2006.01) |
| A61B 6/00 | (2006.01) |
| H04N 13/00 | (2006.01) |
| H04N 13/02 | (2006.01) |
| H04N 13/04 | (2006.01) |
| A61B 5/00 | (2006.01) |
| A61B 8/08 | (2006.01) |

(52) U.S. Cl.
CPC ................. *A61B 8/466* (2013.01); *A61B 6/022* (2013.01); *A61B 6/466* (2013.01); *A61B 8/483* (2013.01); *H04N 13/0014* (2013.01); *H04N 13/0278* (2013.01); *H04N 13/0404* (2013.01); *H04N 13/0447* (2013.01); *H04N 13/0497* (2013.01); *A61B 5/742* (2013.01); *A61B 6/5211* (2013.01); *A61B 6/5229* (2013.01); *A61B 8/5215* (2013.01); *A61B 8/5238* (2013.01); *H04N 13/007* (2013.01); *H04N 13/0438* (2013.01); *H04N 13/0456* (2013.01)

(58) Field of Classification Search
None
See application file for complete search history.

(56) References Cited

U.S. PATENT DOCUMENTS

| 2006/0192776 A1* | 8/2006 | Nomura et al. ............... 345/419 |
| 2010/0238277 A1* | 9/2010 | Takahashi et al. ............. 348/59 |
| 2011/0032339 A1* | 2/2011 | Hirayama et al. .............. 348/51 |

FOREIGN PATENT DOCUMENTS

| CN | 1514300 A | 7/2004 |
| JP | 2005-86414 | 3/2005 |
| JP | 2008113800 A * | 5/2008 |

OTHER PUBLICATIONS

Chinese Office Action issued Apr. 3, 2014, in China Patent Application No. 201210233148.0.

* cited by examiner

*Primary Examiner* — Andrew G Yang
(74) *Attorney, Agent, or Firm* — Oblon, McClelland, Maier & Neustadt, L.L.P.

(57) ABSTRACT

According to one embodiment, an image processing system includes a stereoscopic display device and a control unit. The stereoscopic display device is configured to display a stereoscopic image viewed by an observer stereoscopically by displaying a predetermined parallax number of parallax images. The control unit is configured to perform control, when generating the predetermined parallax number of parallax images from volume data that is three-dimensional medical image data, so as to change a parallactic angle between parallax images based on the shape of a subject portion and to display a predetermined parallax number of parallax images at the parallactic angle thus changed on the stereoscopic display device.

10 Claims, 15 Drawing Sheets

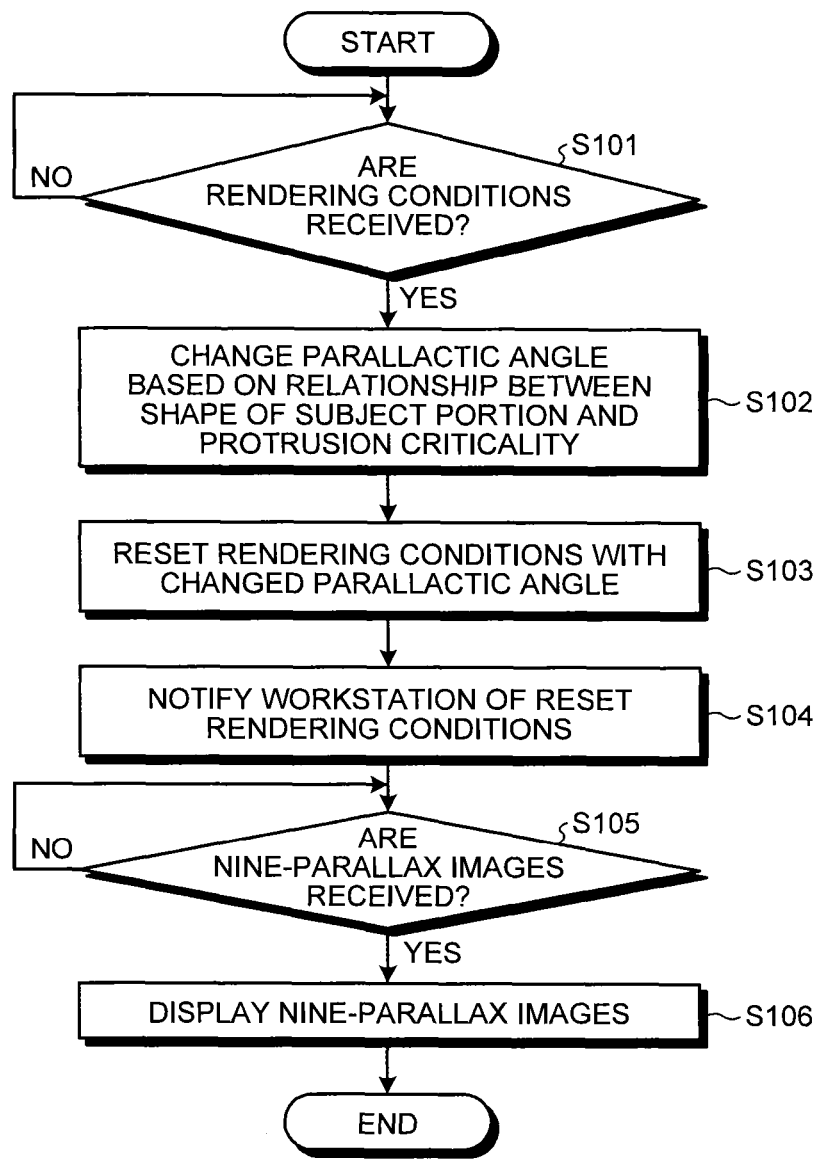

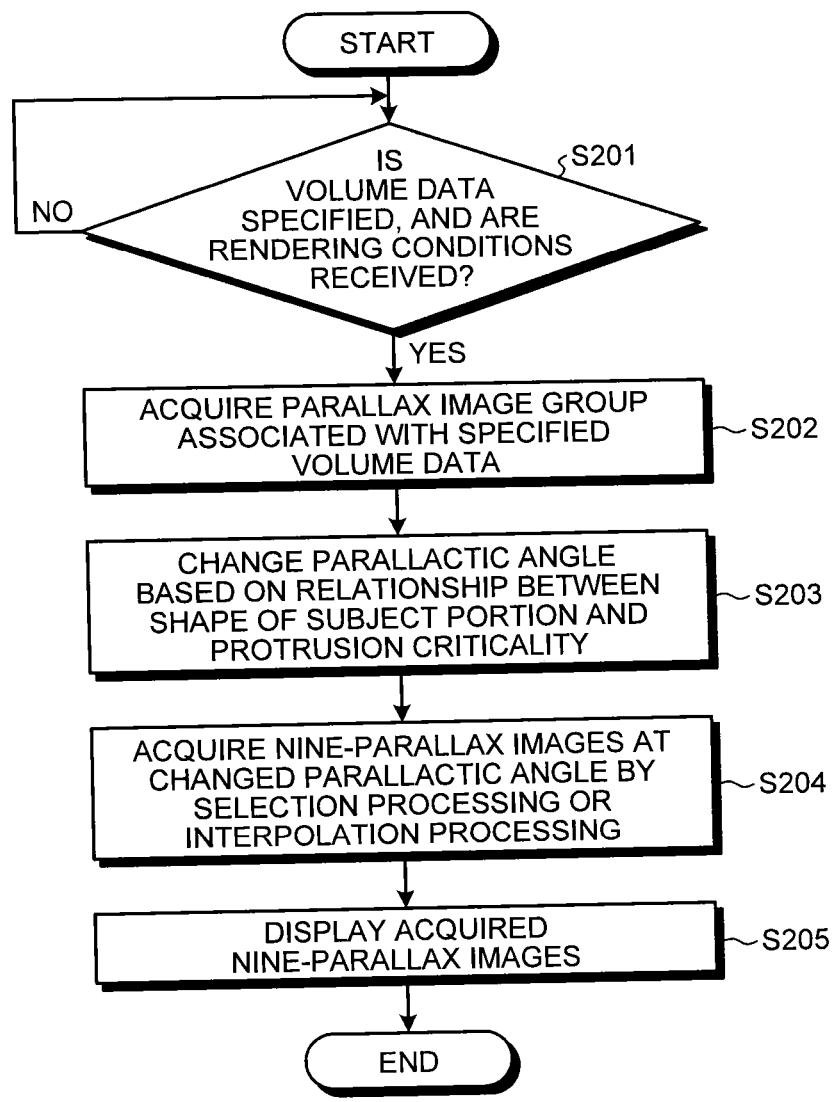

IMAGE PROCESSING SYSTEM, IMAGE PROCESSING APPARATUS, AND IMAGE PROCESSING METHOD

CROSS-REFERENCE TO RELATED APPLICATIONS

This application is based upon and claims the benefit of priority from Japanese Patent Application No. 2011-158254, filed on Jul. 19, 2011; the entire contents of which are incorporated herein by reference.

FIELD

Embodiments described herein relate generally to an image processing system, an image processing apparatus, and an image processing method.

BACKGROUND

Conventionally, monitors enabling an observer to view two-parallax images captured from two viewpoints stereoscopically by using a specific device, such as a pair of stereoscopic-vision glasses, have been in practical use. Furthermore, in recent years, monitors enabling an observer to view multi-parallax images (e.g., nine-parallax images) captured from a plurality of viewpoints stereoscopically with the naked eyes by using a beam control element, such as a lenticular lens, have also been in practical use. Such two-parallax images and nine-parallax images displayed on monitors enabling stereoscopic vision may be generated by estimating depth information of an image captured from one viewpoint and performing image processing using the information thus estimated.

For use in medical image diagnosis apparatuses, such as X-ray computed tomography (CT) apparatuses, magnetic resonance imaging (MRI) apparatuses, and ultrasound diagnosis apparatuses, apparatuses capable of generating three-dimensional medical image data (hereinafter, referred to as volume data) have been in practical use. An arbitrary parallax number of volume rendering images (parallax images) at an arbitrary parallactic angle can be generated from volume data generated by such medical image diagnosis apparatuses. Therefore, it is required to display a two-dimensional volume rendering image generated from volume data stereoscopically on a monitor enabling stereoscopic vision that has been in practical use in recent years.

BRIEF DESCRIPTION OF THE DRAWINGS

FIG. 11 is a flowchart for explaining processing performed by the terminal device included in the image processing system according to the first embodiment;

FIG. 14 is a flowchart for explaining processing performed by a terminal device included in an image processing system according to the second embodiment.

DETAILED DESCRIPTION

According to one embodiment, an image processing system includes a stereoscopic display device and a control unit. The stereoscopic display device is configured to display a stereoscopic image viewed by an observer stereoscopically by displaying a predetermined parallax number of parallax images. The control unit is configured to perform control, when generating the predetermined parallax number of parallax images from volume data that is three-dimensional medical image data, so as to change a parallactic angle between parallax images based on the shape of a subject portion and to display a predetermined parallax number of parallax images at the parallactic angle thus changed on the stereoscopic display device.

Exemplary embodiments of an image processing system and an image processing apparatus are described below in greater detail with reference to the accompanying drawings. In the description below, an image processing system including a workstation having a function as an image processing apparatus will be explained as the embodiments. Terms used in the embodiments below will now be described. A "parallax image group" represents an image group generated by moving a viewpoint position with respect to volume data by a predetermined parallactic angle to perform volume rendering processing. In other words, the "parallax image group" is composed of a plurality of "parallax images" whose "viewpoint positions" are different from one another. A "parallactic angle" represents an angle defined by viewpoint positions adjacent to each other among viewpoint positions set for generating the "parallax image group" and a predetermined position in a space indicated by the volume data (e.g., the center of the space). A "parallax number" represents the number of "parallax images" required for achieving stereoscopic vision on a stereoscopic display monitor. In the description below, "nine-parallax images" represent a "parallax image group" composed of nine "parallax images". Furthermore, in the description below, "two-parallax images" represent a "parallax image group" composed of two "parallax images". A "stereoscopic image" represents an image viewed stereoscopically by an observer who refers to a stereoscopic display monitor that displays a "parallax number" of "parallax images". In other words, the stereoscopic display monitor displays a "parallax number" of "parallax images", thereby displaying the "stereoscopic image" viewed stereoscopically by the observer.

First Embodiment

Figure 1:
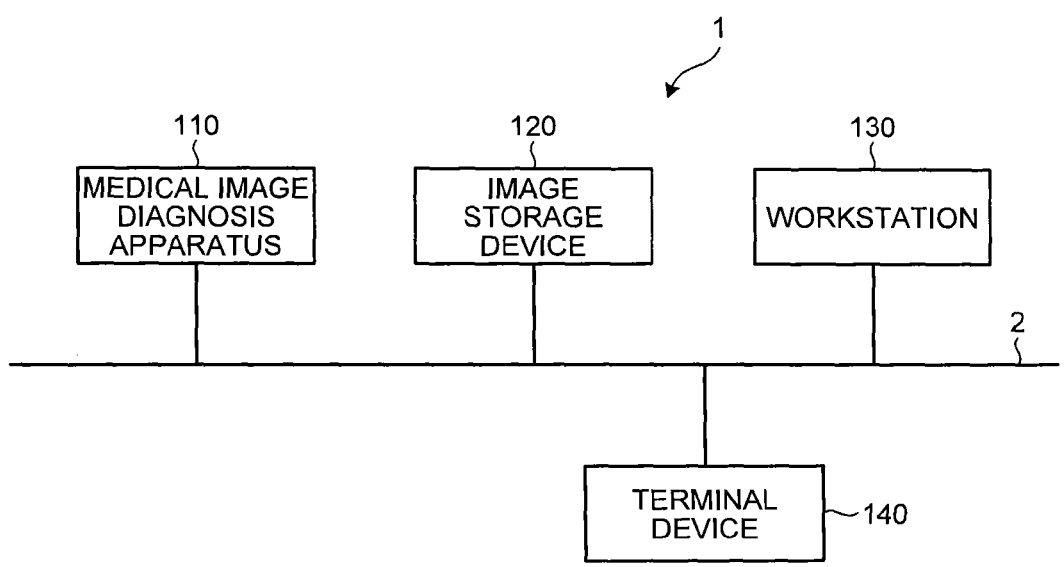
FIG. 1 is a diagram for explaining an exemplary configuration of an image processing system according to a first embodiment.

An exemplary configuration of an image processing system according to a first embodiment will now be described. FIG. 1 is a diagram for explaining the exemplary configuration of the image processing system according to the first embodiment.

As illustrated in FIG. 1, an image processing system 1 according to the first embodiment includes a medical image diagnosis apparatus 110, an image storage device 120, a workstation 130, and a terminal device 140. The devices exemplified in FIG. 1 can communicate with one another directly or indirectly via an in-hospital local area network (LAN) 2 established in a hospital, for example. If a picture archiving and communication system (PACS) is introduced into the image processing system 1, for example, the devices transmit and receive a medical image and the like among one another in accordance with the digital imaging and communications in medicine (DICOM) standard.

The image processing system 1 generates a parallax image group from volume data, which is three-dimensional medical image data generated by the medical image diagnosis apparatus 110, and displays the parallax image group on a monitor enabling stereoscopic vision, thereby providing a medical image capable of being viewed stereoscopically to a doctor or a laboratory technician who works for the hospital. Specifically, in the first embodiment, the workstation 130 performs various types of image processing on the volume data to generate the parallax image group. The workstation 130 and the terminal device 140 have a monitor enabling stereoscopic vision, and display the parallax image group generated by the workstation 130 on the monitor. The image storage device 120 stores therein the volume data generated by the medical image diagnosis apparatus 110 and the parallax image group generated by the workstation 130. In other words, the workstation 130 and the terminal device 140 acquire the volume data and the parallax image group from the image storage device 120 to process the volume image and to display the parallax image group on the monitor. The devices will be explained below in order.

The medical image diagnosis apparatus 110 may be an X-ray diagnosis apparatus, an X-ray CT apparatus, an MRI apparatus, an ultrasound diagnosis apparatus, a single photon emission computed tomography (SPECT) apparatus, a positron emission computed tomography (PET) apparatus, an SPECT-CT apparatus in which an SPECT apparatus and an X-ray CT apparatus are integrated, a PET-CT apparatus in which a PET apparatus and an X-ray CT apparatus are integrated, or a group of these apparatuses. The medical image diagnosis apparatus 110 according to the first embodiment can generate three-dimensional medical image data (volume data).

Specifically, the medical image diagnosis apparatus 110 according to the first embodiment captures a subject to generate volume data. The medical image diagnosis apparatus 110, for example, captures a subject to acquire data, such as projection data and an MR signal, and reconstructs medical image data of a plurality of axial planes in a body axis direction of the subject from the data thus acquired, thereby generating volume data. The medical image diagnosis apparatus 110 reconstructs medical image data of 500 axial planes, for example. The medical image data group of 500 axial planes is volume data. Alternatively, the projection data and the MR signal of the subject captured by the medical image diagnosis apparatus 110 may be used as volume data, for example.

The medical image diagnosis apparatus 110 according to the first embodiment transmits the volume data thus generated to the image storage device 120. When transmitting the volume data to the image storage device 120, the medical image diagnosis apparatus 110 transmits a patient ID for identifying a subject, an examination ID for identifying an examination, an apparatus ID for identifying the medical image diagnosis apparatus 110, and a series ID for identifying single capturing performed by the medical image diagnosis apparatus 110, for example, as additional information.

The image storage device 120 is a database that stores therein medical images. Specifically, the image storage device 120 according to the first embodiment stores the volume data transmitted from the medical image diagnosis apparatus 110 in a storage unit to store the volume data therein. Furthermore, the image storage device 120 according to the first embodiment can store a parallax image group generated from volume data by the workstation 130 in the storage unit to store the parallax image group therein. In this case, the workstation 130 transmits the parallax image group thus generated to the image storage device 120, and the image storage device 120 stores the parallax image group transmitted from the workstation 130 in the storage unit to store the parallax image group therein. In the present embodiment, the workstation 130 and the image storage device 120 exemplified in FIG. 1 may be integrated by using the workstation 130 that can store large-volume images therein. In other words, in the present embodiment, the workstation 130 itself may store therein the volume data or the parallax image group.

In the first embodiment, the volume data and the parallax image group stored in the image storage device 120 are stored therein in a manner corresponding to the patient ID, the examination ID, the apparatus ID, the series ID, and the like. Therefore, the workstation 130 and the terminal device 140 acquire required volume data and a required parallax image group from the image storage device 120 by performing a search using the patient ID, the examination ID, the apparatus ID, the series ID, and the like.

The workstation 130 is an image processing apparatus that performs image processing on a medical image. Specifically, the workstation 130 according to the first embodiment performs various types of rendering processing on volume data acquired from the image storage device 120 to generate a parallax image group. The parallax image group is a plurality of parallax images captured from a plurality of points of view. For example, a parallax image group displayed on a monitor enabling an observer to view nine-parallax images stereoscopically with the naked eyes is nine parallax images whose viewpoint positions are different from one another.

The workstation 130 according to the first embodiment includes a monitor enabling stereoscopic vision (hereinafter, referred to as a stereoscopic display monitor) as a display unit. The workstation 130 generates a parallax image group, and displays the parallax image group thus generated on the stereoscopic display monitor. As a result, an operator of the workstation 130 can perform an operation for generating the parallax image group while checking a medical image that is displayed on the stereoscopic display monitor and capable of being viewed stereoscopically.

The workstation 130 transmits the parallax image group thus generated to the image storage device 120. When transmitting the parallax image group to the image storage device 120, the workstation 130 transmits the patient ID, the examination ID, the apparatus ID, and the series ID, for example, as additional information. Examples of the additional information transmitted when the workstation 130 transmits the parallax image group to the image storage device 120 include additional information related to the parallax image group. Examples of the additional information related to the parallax image group includes the number of parallax images (e.g., "nine"), resolution of the parallax image (e.g., "466 pixels× 350 pixels"), and the like. Furthermore, the workstation 130 can transmit the parallax image group thus generated to the terminal device 140 in response to a request for stereoscopic vision from the terminal device 140.

The workstation 130 according to the first embodiment generates a parallax image group in real time in response to a request from the operator. The workstation 130 according to the first embodiment, for example, generates a parallax image group in response to a request from the operator of the workstation 130. Alternatively, the workstation 130 according to the first embodiment generates a parallax image group in response to a request from an operator of the terminal device 140, which will be described below, and transmits the parallax image group thus generated to the terminal device 140.

The terminal device 140 is a device by which a doctor or a laboratory technician who works for the hospital browses a medical image. The terminal device 140 may be a personal computer (PC), a tablet PC, a personal digital assistant (PDA), or a mobile phone operated by the doctor or the laboratory technician who works for the hospital, for example. Specifically, the terminal device 140 according to the first embodiment includes a stereoscopic display monitor as a display unit. The terminal device 140 acquires a parallax image group from the workstation 130 or the image storage device 120, and displays the parallax image group thus acquired on the stereoscopic display monitor. As a result, the doctor or the laboratory technician who is the observer can browse the medical image capable of being viewed stereoscopically.

The stereoscopic display monitor included in the workstation 130 and the terminal device 140 will now be described. A typical general-purpose monitor in the most widespread use nowadays displays a two-dimensional image two-dimensionally, and fails to display the two-dimensional image stereoscopically. If the observer desires stereoscopic vision on the general-purpose monitor, a device that outputs images to the general-purpose monitor needs to display two-parallax images capable of being viewed stereoscopically by the observer with a parallel method and an intersection method in parallel. Alternatively, the device that outputs images to the general-purpose monitor needs to display an image capable of being viewed stereoscopically by the observer by a complementary color method using a pair of glasses in which red cellophane is attached to a portion for the left eye and blue cellophane is attached to a portion for the right eye, for example.

By contrast, there has been developed a stereoscopic display monitor enabling the observer to view two-parallax images (also referred to as binocular parallax images) stereoscopically by using a specific device, such as a pair of stereoscopic vision glasses.

Figure 2A:
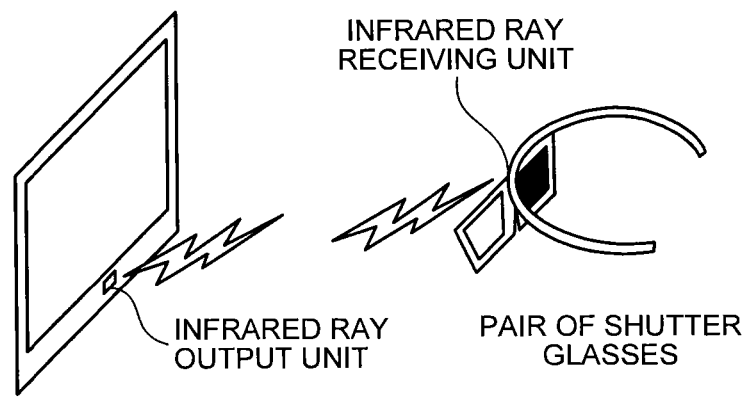
FIG. 2A and FIG. 2B are schematics for explaining an example of a stereoscopic display monitor that performs stereoscopic display using two-parallax images.
Figure 2B:
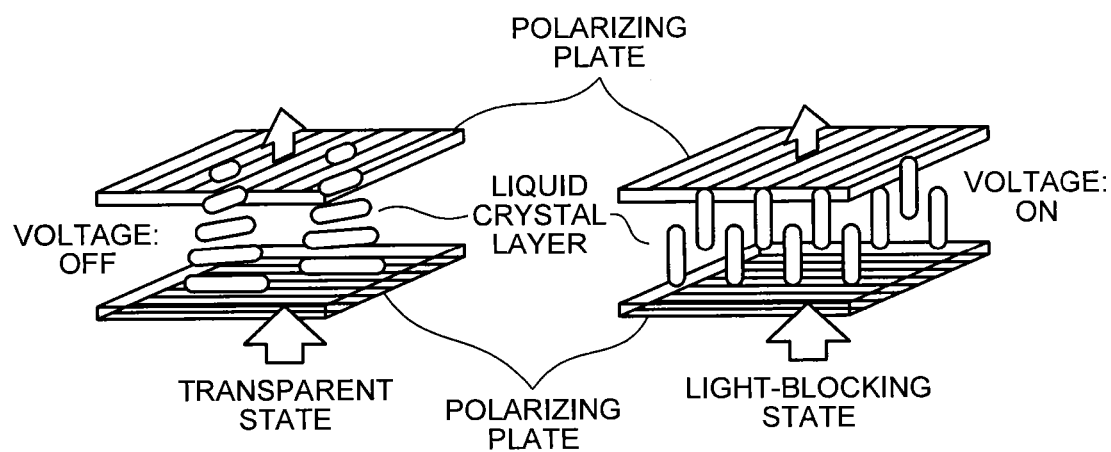

FIG. 2A and FIG. 2B are schematics for explaining an example of a stereoscopic display monitor that performs stereoscopic display using two-parallax images. The example illustrated in FIG. 2A and FIG. 2B is a stereoscopic display monitor that performs stereoscopic display by a shutter method, and a pair of shutter glasses is used as the pair of stereoscopic vision glasses worn by the observer who observes the monitor. The stereoscopic display monitor outputs the two-parallax images alternately on the monitor. The monitor illustrated in FIG. 2A, for example, outputs an image for the left eye and an image for the right eye alternately at 120 Hz. As illustrated in FIG. 2A, the monitor is provided with an infrared ray output unit. The infrared ray output unit controls output of infrared rays in synchronization with an operational timing at which the images are switched.

The infrared rays output from the infrared ray output unit are received by an infrared ray receiving unit of the pair of shutter glasses illustrated in FIG. 2A. A shutter is attached to a left frame and a right frame of the pair of shutter glasses. The pair of shutter glasses switches the state of the left shutter and the right shutter between a transparent state and a light-blocking state alternately in synchronization with an operational timing at which the infrared ray receiving unit receives the infrared rays. The switching processing for the shutter between the transparent state and the light-blocking state will now be described.

As illustrated in FIG. 2B, each of the shutters includes an incident-side polarizing plate, an output-side polarizing plate, and a liquid crystal layer between the incident-side polarizing plate and the output-side polarizing plate. As illustrated in FIG. 2B, the incident-side polarizing plate and the output-side polarizing plate are arranged in a manner orthogonal to each other. As illustrated in FIG. 2B, in an "OFF" state where no voltage is applied, light passing through the incident-side polarizing plate is caused to rotate 90 degrees by an action of the liquid crystal layer and pass through the output-side polarizing plate. In other words, a shutter to which no voltage is applied is in the transparent state.

By contrast, as illustrated in FIG. 2B, in an "ON" state where a voltage is applied, a polarization rotation effect caused by liquid crystal molecules of the liquid crystal layer vanishes, whereby light passing through the incident-side polarizing plate is blocked by the output-side polarizing plate. In other words, a shutter to which a voltage is applied is in the light-blocking state.

Therefore, the infrared ray output unit outputs infrared rays while the image for the left eye is being displayed on the monitor, for example. The infrared ray receiving unit applies no voltage to the left-eye shutter, and applies a voltage to the right-eye shutter while receiving the infrared rays. Thus, as illustrated in FIG. 2A, the right-eye shutter is in the light-blocking state, and the left-eye shutter is in the transparent state, whereby the image for the left eye is incident on the left eye of the observer. By contrast, the infrared ray output unit stops output of the infrared rays while the image for the right eye is being displayed on the monitor. The infrared ray receiving unit applies no voltage to the right-eye shutter, and applies a voltage to the left-eye shutter while receiving no infrared ray. Thus, the left-eye shutter is in the light-blocking state, and the right-eye shutter is in the transparent state, whereby the image for the right eye is incident on the right eye of the observer. As described above, the stereoscopic display monitor illustrated in FIG. 2A and FIG. 2B switches the images displayed on the monitor in synchronization with the states of the shutters, thereby displaying an image capable of being viewed stereoscopically by the observer. In terms of a stereoscopic display monitor enabling the observer to view two-parallax images stereoscopically, a monitor employing a polarizing glasses method is also known in addition to the monitor employing the shutter method described above.

Furthermore, examples of a stereoscopic display monitor that has been put to practical use in recent years include a monitor enabling an observer to view multi-parallax images, such as nine-parallax images, stereoscopically with the naked eyes by using a beam control element, such as a lenticular lens. Such a stereoscopic display monitor enables stereoscopic vision by binocular parallax and stereoscopic vision by motion parallax in which video to be observed changes in association with movement of the viewpoint of the observer.

Figure 3:
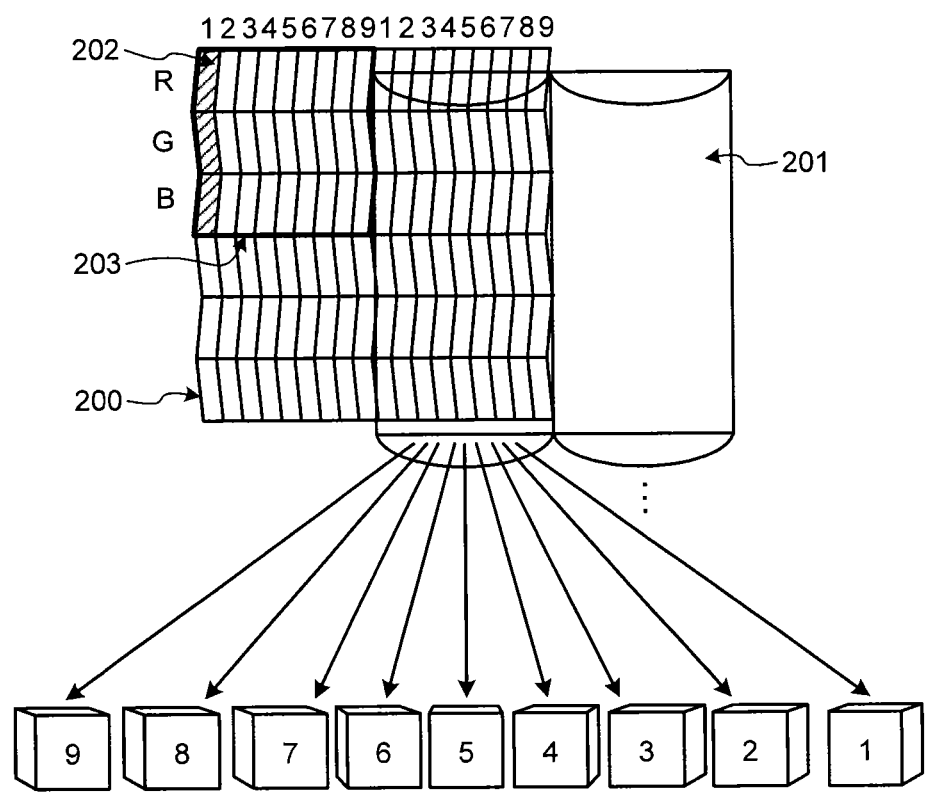
FIG. 3 is a schematic for explaining an example of a stereoscopic display monitor that performs stereoscopic display using nine-parallax images.

FIG. 3 is a schematic for explaining an example of a stereoscopic display monitor that performs stereoscopic display using nine-parallax images. In the stereoscopic display monitor illustrated in FIG. 3, a beam control element is arranged in front of a display surface 200 in a planar shape, such as a liquid crystal panel. In the stereoscopic display monitor illustrated in FIG. 3, for example, a vertical lenticular sheet 201 whose optical aperture extends in the vertical direction is attached to the front of the display surface 200 as the beam control element. In the example illustrated in FIG. 3, the vertical lenticular sheet 201 is attached such that a convex portion thereof faces the front. Alternatively, the vertical lenticular sheet 201 may be attached such that the convex portion thereof faces the display surface 200.

As illustrated in FIG. 3, pixels 202 whose aspect ratio is 3 to 1 and in which three sub pixels of red (R), green (G), and blue (B) are aligned in the longitudinal direction are arranged in a matrix manner. The stereoscopic display monitor illustrated in FIG. 3 converts nine-parallax images composed of nine images into an intermediate image in which the nine-parallax images are arranged in a predetermined format (e.g., a grid pattern), and outputs the intermediate image to the display surface 200. The nine-parallax images, for example, are converted into an intermediate image in a format of a grid pattern in which the nine images are arranged in "three rows and three columns", and are output to the display surface 200. In other words, the stereoscopic display monitor illustrated in FIG. 3 allocates nine pixels in the same position in the nine-parallax images to the pixels 202 of nine columns, and outputs the nine pixels. The pixels 202 of nine columns are a unit pixel group 203 that displays nine images whose viewpoint positions are different from one another simultaneously.

The nine-parallax images output simultaneously as the unit pixel group 203 on the display surface 200 are emitted as parallel light by a light emitting diode (LED) backlight, for example, and are emitted in multi-directions by the vertical lenticular sheet 201. Light of each pixel in the nine-parallax images is emitted in multi-directions, whereby light incident on the right eye and the left eye of the observer changes in association with the position of the observer (position of the viewpoint). In other words, the parallax image incident on the right eye and the parallax image incident on the left eye have different parallactic angles depending on the viewing angle of the observer. As a result, the observer can view a captured subject stereoscopically at each of the nine positions illustrated in FIG. 3, for example. Furthermore, the observer can view the captured subject stereoscopically in a manner facing the captured subject at the position of "5" illustrated in FIG. 3, and can view the captured subject stereoscopically such that the position of the captured subject is changed at each of the positions other than "5" illustrated in FIG. 3, for example. The stereoscopic display monitor illustrated in FIG. 3 is just an example. The stereoscopic display monitor that displays nine-parallax images may be a horizontal stripe liquid crystal of "RRR . . . , GGG . . . , BBB . . . " as illustrated in FIG. 3, or may be a vertical stripe liquid crystal of "RGBRGB . . . ". The stereoscopic display monitor illustrated in FIG. 3 may employ a vertical lens method in which the lenticular sheet is arranged vertically as illustrated in FIG. 3, or may employ an oblique lens method in which the lenticular sheet is arranged obliquely. The format of the intermediate image is not limited to the grid pattern of "three rows and three columns". The format of the intermediate image may be an arbitrary format in accordance with the specifications of the monitor, such as "one row and nine columns" or "nine rows and one column", for example.

The stereoscopic display monitor explained with respect to FIG. 2A and FIG. 2B is hereinafter referred to as a two-parallax monitor. The stereoscopic display monitor explained with respect to FIG. 3 is hereinafter referred to as a nine-parallax monitor. In other words, the two-parallax monitor is a stereoscopic display device that enables stereoscopic vision by binocular parallax. The nine-parallax monitor is a stereoscopic display device that enables stereoscopic vision by binocular parallax and that can change the image observed by the observer depending on "movement of the viewpoint of the observer (motion parallax)" by displaying nine images (nine-parallax images) simultaneously.

The explanation has been made of the exemplary configuration of the image processing system 1 according to the first embodiment. Application of the image processing system 1 is not limited to the case where the PACS is introduced. The image processing system 1 is also applied to the case where an electronic chart system for managing electronic charts to which medical images are attached is introduced, for example. In this case, the image storage device 120 corresponds to a database that stores therein the electronic charts. Furthermore, the image processing system 1 is also applied to the case where a hospital information system (HIS) or a radiology information system (RIS) is introduced, for example. The configuration of the image processing system 1 is not limited to the exemplary configuration described above. Functions of each device and assignation thereof may be changed as appropriate depending on aspects of operations.

Figure 4:
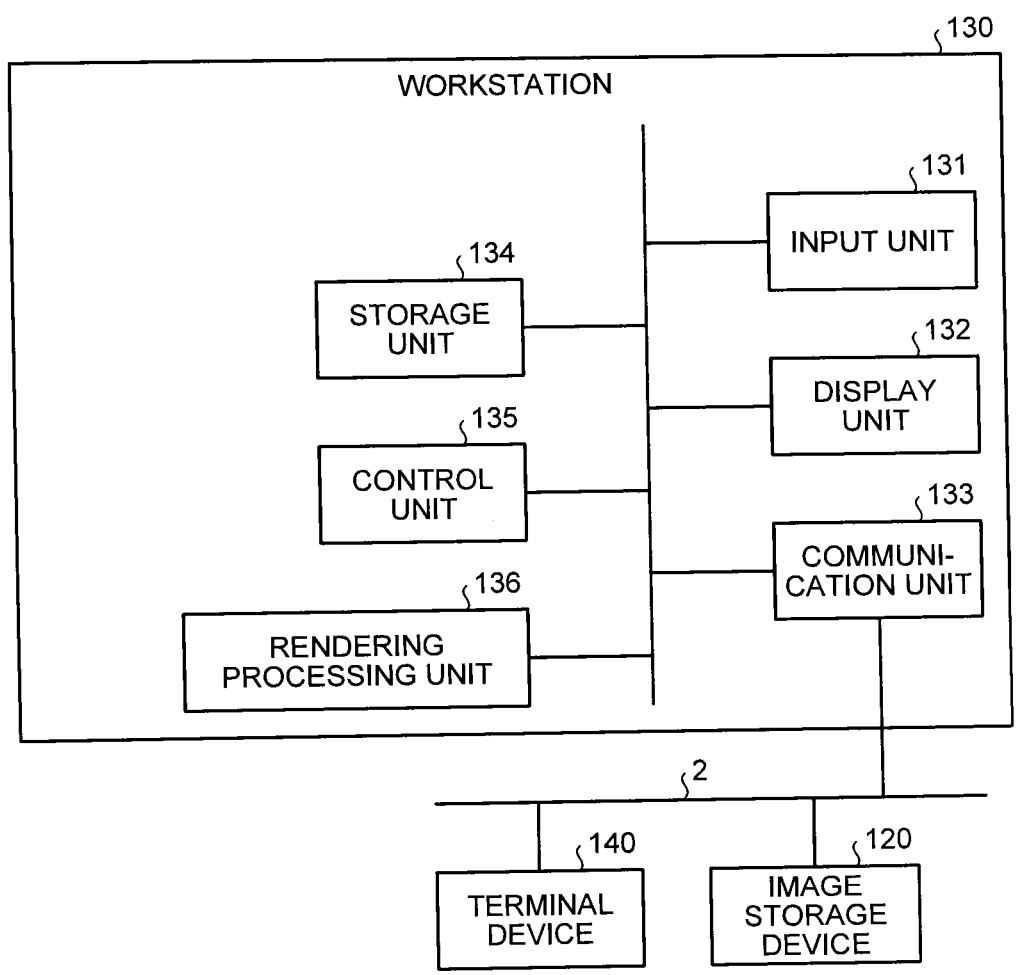
FIG. 4 is a diagram for explaining an exemplary configuration of a workstation according to the first embodiment.

An exemplary configuration of the workstation according to the first embodiment will now be described with reference to FIG. 4. FIG. 4 is a diagram for explaining the exemplary configuration of the workstation according to the first embodiment. In the description below, a "parallax image group" represents an image group for stereoscopic vision (a volume rendering image group) generated by performing volume rendering processing on volume data. A "parallax image" represents an individual image constituting the "parallax image group". In other words, the "parallax image group" is composed of a plurality of "parallax images" whose viewpoint positions are different from one another.

The workstation 130 according to the first embodiment is a sophisticated computer suitable for image processing and the like, and includes an input unit 131, a display unit 132, a communication unit 133, a storage unit 134, a control unit 135, and a rendering processing unit 136. An explanation will be made of the case where the workstation 130 is a sophisticated computer suitable for image processing and the like. However, the workstation 130 is not limited thereto, and may be an arbitrary information processing apparatus. The workstation 130 may be an arbitrary personal computer, for example.

The input unit 131 is a mouse, a keyboard, and a trackball, for example, and receives input of various types of operations from the operator to the workstation 130. Specifically, the input unit 131 according to the first embodiment receives input of information used for acquiring volume data to be a target of rendering processing from the image storage device 120. The input unit 131 receives input of a patient ID, an examination ID, an apparatus ID, and a series ID, for example. Furthermore, the input unit 131 according to the first embodiment receives input of conditions related to rendering processing (rendering conditions).

The display unit 132 is a liquid crystal panel as a stereoscopic display monitor, for example, and displays various types of information. Specifically, the display unit 132 according to the first embodiment displays a graphical user interface (GUI) for receiving various types of operations from the operator, a parallax image group, and the like. The display unit 132 is a two-parallax monitor or a nine-parallax monitor, for example. An explanation will be made of the case where the display unit 132 is a nine-parallax monitor. The communication unit 133 is a network interface card (NIC), for example, and performs communications with other devices.

The storage unit 134 is a hard disk or a semiconductor memory element, for example, and stores therein various types of information. Specifically, the storage unit 134 according to the first embodiment stores therein volume data acquired from the image storage device 120 via the communication unit 133. Furthermore, the storage unit 134 according to the first embodiment stores therein volume data being subjected to rendering processing, a parallax image group generated by the rendering processing, and other information.

The control unit 135 is an electronic circuit, such as a central processing unit (CPU) and a micro processing unit (MPU), or an integrated circuit, such as an application specific integrated circuit (ASIC) and a field programmable gate array (FPGA), for example, and controls the workstation 130 collectively.

The control unit 135 according to the first embodiment, for example, controls display of the GUI and display of a parallax image group on the display unit 132. The control unit 135, for example, controls transmission and reception of volume data and a parallax image group to and from the image storage device 120 via the communication unit 133. The control unit 135, for example, controls rendering processing performed by the rendering processing unit 136. The control unit 135, for example, controls reading of volume data from the storage unit 134 and storing of a parallax image group in the storage unit 134.

The rendering processing unit 136 performs various types of rendering processing on volume data acquired from the image storage device 120 under the control of the control unit 135 to generate a parallax image group. Specifically, the rendering processing unit 136 according to the first embodiment reads volume data from the storage unit 134, and performs preprocessing on the volume data first. The rendering processing unit 136 then performs volume rendering processing on the volume data subjected to the preprocessing to generate a parallax image group. Subsequently, the rendering processing unit 136 generates a two-dimensional image on which various types of information (e.g., a scale, a patient's name, and an examination item) are depicted, and superimposes the two-dimensional image on each image of the parallax image group, thereby generating a two-dimensional image to be output. The rendering processing unit 136 then stores the parallax image group thus generated and the two-dimensional image to be output in the storage unit 134. In the first embodiment, the rendering processing represents the entire image processing performed on volume data, and the volume rendering processing represents processing for generating a two-dimensional image on which three-dimensional information is reflected in the rendering processing. A medical image generated by the rendering processing corresponds to a parallax image, for example.

Figure 5:
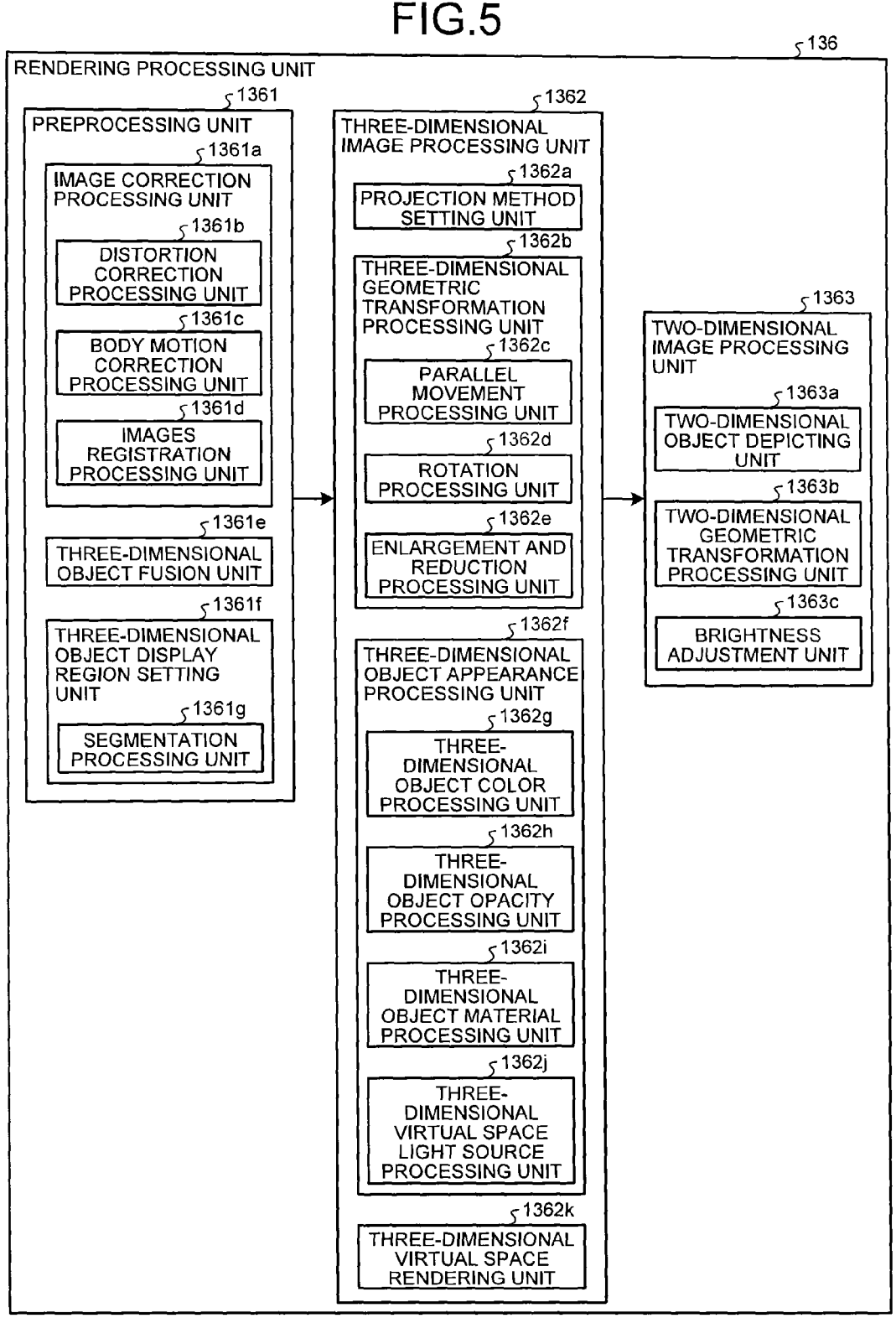
FIG. 5 is a diagram for explaining an exemplary configuration of a rendering processing unit illustrated in FIG. 4.

FIG. 5 is a diagram for explaining an exemplary configuration of the rendering processing unit illustrated in FIG. 4. As illustrated in FIG. 5, the rendering processing unit 136 includes a preprocessing unit 1361, a three-dimensional image processing unit 1362, and a two-dimensional image processing unit 1363. The preprocessing unit 1361 performs preprocessing on volume data. The three-dimensional image processing unit 1362 generates a parallax image group from the volume data subjected to the preprocessing. The two-dimensional image processing unit 1363 generates a two-dimensional image to be output that is obtained by superimposing various types of information on the parallax image group. The units will be explained below in order.

The preprocessing unit 1361 is a processing unit that performs various types of preprocessing when rendering processing is performed on volume data, and includes an image correction processing unit 1361a, a three-dimensional object fusion unit 1361e, and a three-dimensional object display region setting unit 1361f.

The image correction processing unit 1361a is a processing unit that performs image correction processing when two types of volume data are processed as one piece of volume data, and includes a distortion correction processing unit 1361b, a body motion correction processing unit 1361c, and an images registration processing unit 1361d as illustrated in FIG. 5. The image correction processing unit 1361a performs image correction processing when volume data of a PET image and volume data of an X-ray CT image generated by a PET-CT apparatus are processed as one piece of volume data, for example. Alternatively, the image correction processing unit 1361a performs image correction processing when volume data of a T1-weighted image and volume data of a T2-weighted image generated by an MRI apparatus are processed as one piece of volume data.

The distortion correction processing unit 1361b corrects distortion of data in individual volume data caused by acquisition conditions in data acquisition performed by the medical image diagnosis apparatus 110. The body motion correction processing unit 1361c corrects movement caused by body motion of the subject during a time period for acquiring data used for generating individual volume data. The images registration processing unit 1361d performs registration using a cross-correlation method, for example, between two pieces of volume data on which the correction processing is performed by the distortion correction processing unit 1361b and the body motion correction processing unit 1361c.

The three-dimensional object fusion unit 1361e fuses a plurality of pieces of volume data on which registration is performed by the images registration processing unit 1361d. The processing performed by the image correction processing unit 1361a and the three-dimensional object fusion unit 1361e is omitted if rendering processing is performed on a single piece of volume data.

The three-dimensional object display region setting unit 1361f is a processing unit that sets a display region corresponding to an organ to be displayed that is specified by the operator, and includes a segmentation processing unit 1361g. The segmentation processing unit 1361g is a processing unit that extracts an organ, such as a heart, a lung, and a blood vessel, specified by the operator with a region growing method based on the pixel value of volume data (voxel value), for example.

If the operator specifies no organ to be displayed, the segmentation processing unit 1361g performs no segmentation processing. By contrast, if the operator specifies a plurality of organs to be displayed, the segmentation processing unit 1361g extracts a plurality of organs corresponding thereto. The processing of the segmentation processing unit 1361g may be performed again in response to a request for fine adjustment made by the operator who refers to a rendering image.

The three-dimensional image processing unit 1362 performs volume rendering processing on the volume data on which the preprocessing is performed by the preprocessing unit 1361. The three-dimensional image processing unit 1362 serves as a processing unit that performs volume rendering processing, and includes a projection method setting unit

1362a, a three-dimensional geometric transformation processing unit 1362b, a three-dimensional object appearance processing unit 1362f, and a three-dimensional virtual space rendering unit 1362k.

The projection method setting unit 1362a determines a projection method for generating a parallax image group. The projection method setting unit 1362a determines whether the volume rendering processing is performed by a parallel projection method or a perspective projection method, for example.

The three-dimensional geometric transformation processing unit 1362b is a processing unit that determines information used for three-dimensionally geometrically transforming volume data on which the volume rendering processing is to be performed, and includes a parallel movement processing unit 1362c, a rotation processing unit 1362d, an enlargement and reduction processing unit 1362e. The parallel movement processing unit 1362c is a processing unit that determines a movement amount by which the volume data is moved in a parallel manner if the viewpoint position is moved in a parallel manner when the volume rendering processing is being performed. The rotation processing unit 1362d is a processing unit that determines a movement amount by which the volume data is moved rotationally if the viewpoint position is moved rotationally when the volume rendering processing is being performed. The enlargement and reduction processing unit 1362e is a processing unit that determines an enlargement ratio and a reduction ratio of the volume data if enlargement and reduction of the parallax image group is requested.

The three-dimensional object appearance processing unit 1362f includes a three-dimensional object color processing unit 1362g, a three-dimensional object opacity processing unit 1362h, a three-dimensional object material processing unit 1362i, and a three-dimensional virtual space light source processing unit 1362j. The three-dimensional object appearance processing unit 1362f performs processing for determining a display aspect of the parallax image group to be displayed by these processing units in response to a request made by the operator, for example.

The three-dimensional object color processing unit 1362g is a processing unit that determines a color applied to each region segmented in the volume data. The three-dimensional object opacity processing unit 1362h is a processing unit that determines the opacity of each voxel constituting each region segmented in the volume data. A region behind a region whose opacity is determined to be "100%" in the volume data is not depicted in the parallax image group. Furthermore, a region whose opacity is determined to be "0%" in the volume data is not depicted in the parallax image group.

The three-dimensional object material processing unit 1362i is a processing unit that determines a material of each region segmented in the volume data to adjust texture when the region is depicted. The three-dimensional virtual space light source processing unit 1362j is a processing unit that determines a position of a virtual light source arranged in a three-dimensional virtual space and a type of the virtual light source when the volume rendering processing is performed on the volume data. Examples of the type of the virtual light source include a light source that emits parallel light beams from infinity and a light source that emits radial light beams from the viewpoint.

The three-dimensional virtual space rendering unit 1362k performs volume rendering processing on volume data to generate a parallax image group. To perform the volume rendering processing, the three-dimensional virtual space rendering unit 1362k uses various types of information determined by the projection method setting unit 1362a, the three-dimensional geometric transformation processing unit 1362b, and the three-dimensional object appearance processing unit 1362f as needed.

The volume rendering processing is performed by the three-dimensional virtual space rendering unit 1362k in accordance with rendering conditions. Examples of the rendering conditions include "the parallel projection method" and "the perspective projection method". Examples of the rendering conditions also include "a reference viewpoint position and a parallactic angle". Examples of the rendering conditions also include "parallel movement of the viewpoint position", "rotational movement of the viewpoint position", "enlargement of the parallax image group", and "reduction of the parallax image group". Examples of the rendering conditions also include "a color to be applied", "transmittance", "texture", "the position of the virtual light source", and "the type of the virtual light source". Such rendering conditions may be received from the operator via the input unit 131, or may be set by default. In both cases, the three-dimensional virtual space rendering unit 1362k receives the rendering conditions from the control unit 135, and performs the volume rendering processing on the volume data in accordance with the rendering conditions. At this time, the projection method setting unit 1362a, the three-dimensional geometric transformation processing unit 1362b, and the three-dimensional object appearance processing unit 1362f determine required various types of information in accordance with the rendering conditions. As a result, the three-dimensional virtual space rendering unit 1362k uses the various types of information thus determined to generate the parallax image group.

Figure 6A:
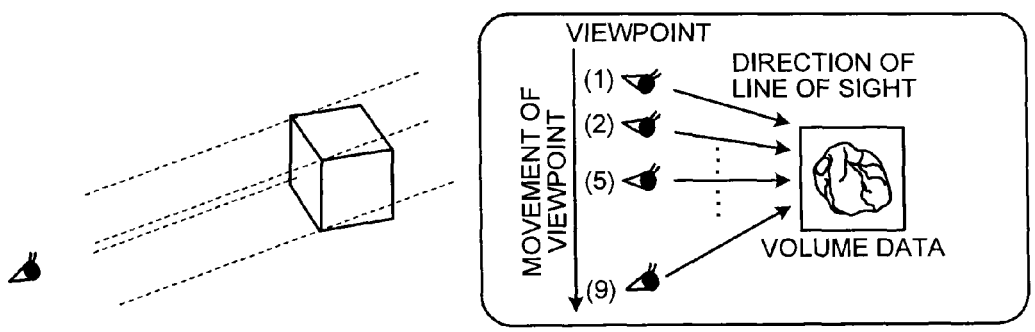
FIG. 6A, FIG. 6B, and FIG. 6C are schematics for explaining an example of volume rendering processing according to the first embodiment.
Figure 6B:
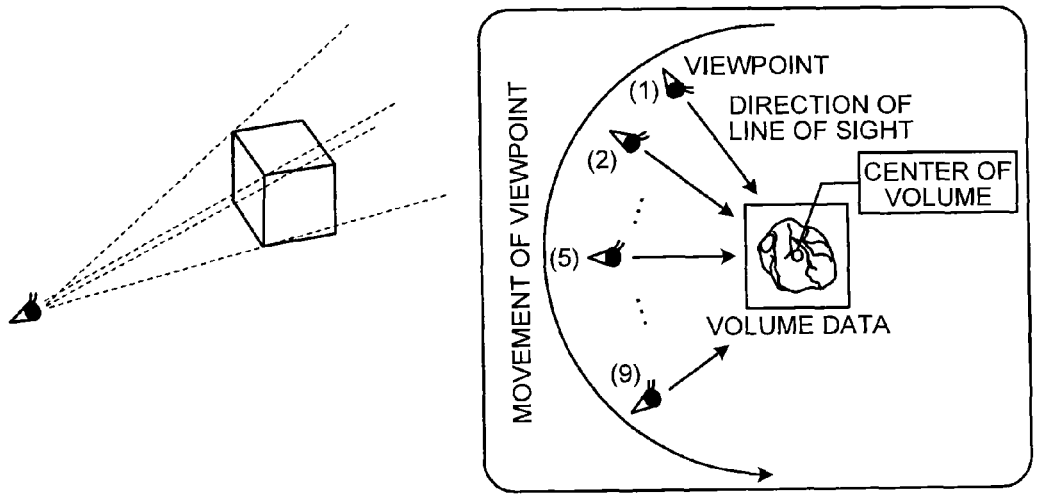
Figure 6C:
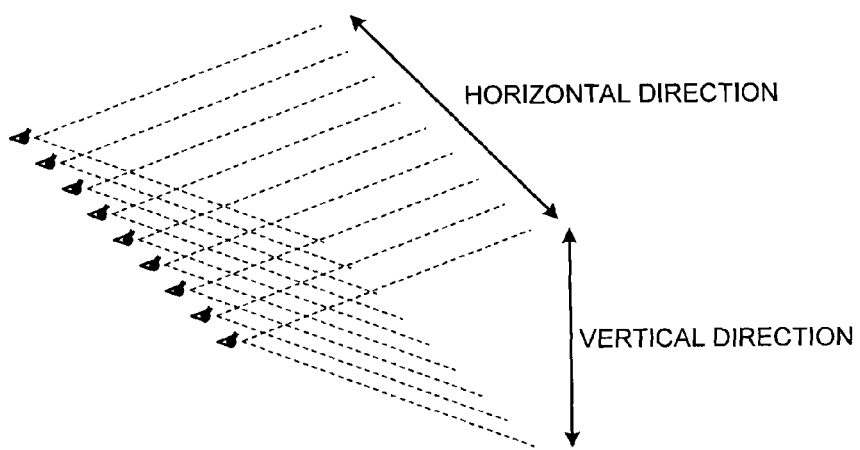

FIG. 6A, FIG. 6B, and FIG. 6C are schematics for explaining an example of volume rendering processing according to the first embodiment. An assumption is made that the three-dimensional virtual space rendering unit 1362k receives the parallel projection method, and receives a reference viewpoint position (5) and a parallactic angle of "one degree" as the rendering conditions as illustrated in FIG. 6A, for example. In this case, the three-dimensional virtual space rendering unit 1362k sets a light source that emits parallel light beams from infinity along a direction of a line of sight as illustrated in FIG. 6A. The three-dimensional virtual space rendering unit 1362k then moves the position of the viewpoint from (1) to (9) in a parallel manner by a parallactic angle of "one degree". Thus, the three-dimensional virtual space rendering unit 1362k generates nine parallax images whose parallactic angles (angles between the directions of the lines of sight) are set to one degree by the parallel projection method.

Alternatively, an assumption is made that the three-dimensional virtual space rendering unit 1362k receives the perspective projection method, and receives a reference viewpoint position (5) and a parallactic angle of "one degree" as the rendering conditions as illustrated in FIG. 6B. In this case, the three-dimensional virtual space rendering unit 1362k sets a point light source or a surface light source that emits light in a three-dimensionally radial manner about the direction of the line of sight for each viewpoint as illustrated in FIG. 6B. The three-dimensional virtual space rendering unit 1362k then moves the position of the viewpoint from (1) to (9) rotationally by a parallactic angle of "one degree" about the center (the center of gravity) of a section of the volume data, for example. Thus, the three-dimensional virtual space rendering unit 1362k generates nine parallax images whose parallactic angles are set to one degree by the perspective projection method. If the perspective projection method is employed, the viewpoints (1) to (9) may be realized by parallel movement depending on the rendering conditions. As illustrated in FIG.

6A and FIG. 6B, the direction of the line of sight is a direction toward the center (the center of gravity) of a section of the volume data from the viewpoint.

Still alternatively, as illustrated in FIG. 6C, the three-dimensional virtual space rendering unit 1362k sets a light source that emits light in a two-dimensionally radial manner about the direction of the line of sight with respect to the vertical direction of the displayed volume rendering image and emits parallel light beams from infinity along the direction of the line of sight with respect to the horizontal direction of the displayed volume rendering image. Thus, the three-dimensional virtual space rendering unit 1362k may perform volume rendering processing by combining the parallel projection method and the perspective projection method.

The nine parallax images thus generated is a parallax image group. In the first embodiment, for example, the nine parallax images are converted into an intermediate image in which the nine-parallax images are arranged in a predetermined format (e.g., a grid pattern) by the control unit 135, and are output to the display unit 132 serving as a stereoscopic display monitor. As a result, the operator of the workstation 130 can perform an operation for generating the parallax image group while checking the medical image that is displayed on the stereoscopic display monitor and capable of being viewed stereoscopically.

In the example illustrated in FIG. 6A, FIG. 6B, and FIG. 6C, the explanation has been made of the case where the projection method, and the reference viewpoint position and the parallactic angle are received as the rendering conditions. However, if other conditions are received as the rendering conditions, the three-dimensional virtual space rendering unit 1362k also generates a parallax image group while reflecting each rendering condition.

Furthermore, the three-dimensional virtual space rendering unit 1362k has a function to perform multi planer reconstruction (MPR) to reconstruct an MPR image from volume data in addition to volume rendering. The three-dimensional virtual space rendering unit 1362k also has a function to perform "curved MPR" and a function to perform "intensity projection".

Subsequently, the parallax image group generated from the volume data by the three-dimensional image processing unit 1362 is used as an underlay. By superimposing an overlay on which various types of information (e.g., a scale, a patient's name, and an examination item) are superimposed on the underlay, a two-dimensional image to be output is generated. The two-dimensional image processing unit 1363 is a processing unit that generates a two-dimensional image to be output by performing image processing on an overlay and an underlay, and includes a two-dimensional object depicting unit 1363a, a two-dimensional geometric transformation processing unit 1363b, and a brightness adjustment unit 1363c as illustrated in FIG. 5. To reduce load required for generating the two-dimensional image to be output, for example, the two-dimensional image processing unit 1363 superimposes one overlay on each of the nine parallax images (underlays), thereby generating nine two-dimensional images to be output.

The two-dimensional object depicting unit 1363a is a processing unit that depicts various types of information to be depicted on an overlay. The two-dimensional geometric transformation processing unit 1363b is a processing unit that performs parallel movement processing or rotational movement processing on the positions of the various types of information depicted on the overlay and that performs enlargement processing or reduction processing on the various types of information depicted on the overlay.

The brightness adjustment unit 1363c is a processing unit that performs brightness transformation processing and that adjusts the brightness of an overlay and an underlay depending on parameters for image processing, such as gradation of the stereoscopic display monitor to which the two-dimensional image is output, the window width (WW), and the window level (WL), for example.

The two-dimensional images to be output that are generated in this manner are stored in the storage unit 134 by the control unit 135, for example, and are transmitted to the image storage device 120 via the communication unit 133. If the terminal device 140 acquires the two-dimensional images to be output from the image storage device 120, converts the two-dimensional images into an intermediate image in which the two-dimensional images are arranged in a predetermined format (e.g., a grid pattern), and displays the intermediate image on the stereoscopic display monitor, for example, the doctor or the laboratory technician who is the observer can browse the medial image capable of being viewed stereoscopically with the various types of information (e.g., a scale, a patient's name, and an examination item) depicted thereon. Alternatively, the two-dimensional images to be output are transmitted to the terminal device 140 directly by the control unit 135 via the communication unit 133, for example.

Figure 7:
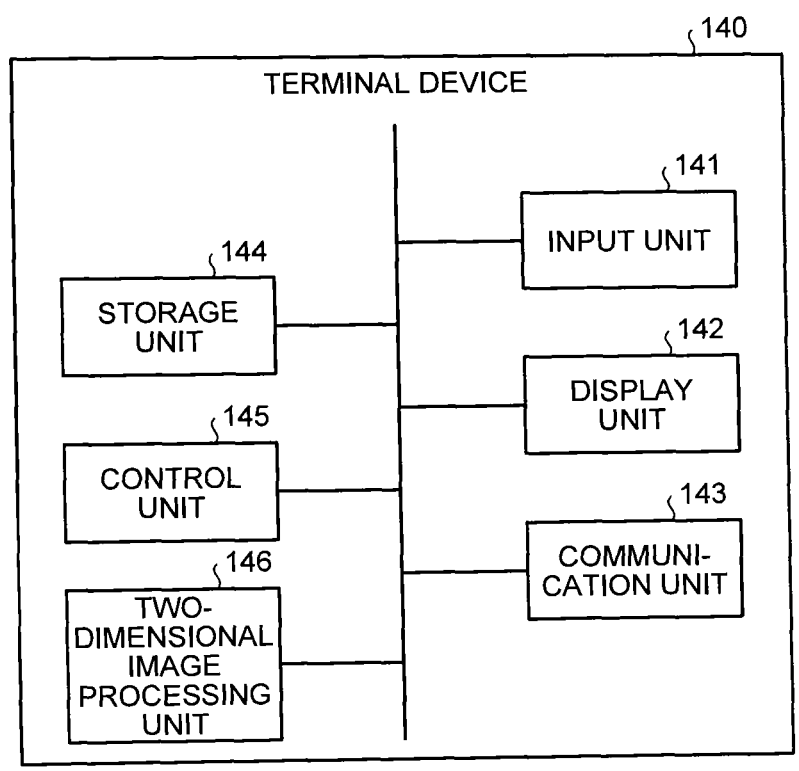
FIG. 7 is a diagram for explaining an exemplary configuration of a terminal device according to the first embodiment.

The terminal device 140 according to the first embodiment is a device by which a doctor or a laboratory technician who works for the hospital browses a medical image as described above, and acquires the parallax image group (two-dimensional images to be output) generated by the rendering processing unit 136 from the image storage device 120 or the workstation 130. FIG. 7 is a diagram for explaining an exemplary configuration of the terminal device according to the first embodiment.

As illustrated in FIG. 7, the terminal device 140 according to the first embodiment includes an input unit 141, a display unit 142, a communication unit 143, a storage unit 144, a control unit 145, and a two-dimensional image processing unit 146.

The input unit 141 is a mouse, a keyboard, and a trackball, for example, and receives input of various types of operations from the operator to the terminal device 140. Specifically, the input unit 141 according to the first embodiment receives a request for stereoscopic vision from the operator. The input unit 141, for example, receives a patient ID, an examination ID, an apparatus ID, and a series ID for specifying volume data requested to be displayed for radiogram interpretation by the operator as the request for stereoscopic vision. Furthermore, for example, the input unit 141 receives rendering conditions for volume data desired to be displayed for interpretation by the operator as a request for stereoscopic vision.

The display unit 142 is a liquid crystal panel as a stereoscopic display monitor, for example, and displays various types of information. Specifically, the display unit 142 according to the first embodiment displays a GUI for receiving various types of operations from the operator, a stereoscopic image, and the like. The display unit 142 is a two-parallax monitor or a nine-parallax monitor, for example. An explanation will be made of the case where the display unit 142 is a nine-parallax monitor.

The communication unit 143 is a NIC, for example, and performs communications with other devices. The communication unit 143 according to the first embodiment, for example, transmits the information related to the request for stereoscopic vision received by the input unit 141 to the image storage device 120. Furthermore, the communication unit 143 according to the first embodiment receives a parallax image group and the like transmitted from the image storage device 120 or the workstation 130 in response to the request for stereoscopic vision.

The storage unit 144 is a hard disk or a semiconductor memory element, for example, and stores therein various types of information. Specifically, the storage unit 144 according to the first embodiment stores therein a parallax image group and the like acquired from the image storage device 120 or the workstation 130 via the communication unit 143. Furthermore, the storage unit 144 stores therein additional information (e.g., the parallax number and the resolution) of the parallax image group acquired from the image storage device 120 or the workstation 130 via the communication unit 143.

The control unit 145 is an electronic circuit, such as a CPU and an MPU, or an integrated circuit, such as an ASIC and an FPGA, and controls the terminal device 140 collectively.

The control unit 145, for example, controls transmission and reception of information on a request for stereoscopic vision to and from the image storage device 120 via the communication unit 143. In addition, the control unit 145 controls transmission and reception of a parallax image group and the like to and from the image storage device 120 or the workstation 130 via the communication unit 143. Furthermore, the control unit 145, for example, controls storing of a parallax image group and the like in the storage unit 144 and reading of a parallax image group and the like from the storage unit 144.

The control unit 145 according to the first embodiment controls display of the GUI and display of a parallax image group on the display unit 142. The control unit 145 according to the first embodiment converts the parallax image group into an intermediate image in which the parallax image group is arranged in a predetermined format (e.g., a grid pattern), and outputs the intermediate image to the display unit 142, which is a nine-parallax monitor.

Furthermore, the control unit 145 according to the first embodiment controls image processing performed by the two-dimensional image processing unit 146.

The two-dimensional image processing unit 146 has the same function as that of the two-dimensional image processing unit 1363 explained with reference to FIG. 5. In other words, the two-dimensional image processing unit 146 generates overlays, and superimposes the overlays on the parallax image group serving as underlays generated by the three-dimensional image processing unit 1362, thereby generating two-dimensional images to be output to the display unit 142.

Furthermore, the two-dimensional image processing unit 146 according to the first embodiment has an interpolation function to generate a new parallax image from two parallax images by interpolation processing using depth information of each of the two parallax images. The interpolation function of the two-dimensional image processing unit 146 will be described later in detail.

As described above, the rendering processing unit 136 generates a parallax image group from volume data under the control of the control unit 135. The control unit 135, for example, acquires additional information of volume data specified by the operator of the terminal device 140 and rendering conditions for the volume data via the communication unit 143 and the communication unit 133. Subsequently, for example, the control unit 135 acquires the volume data thus specified from the image storage device 120, and causes the rendering processing unit 136 to perform volume rendering processing on the volume data thus acquired in accordance with the rendering conditions acquired from the terminal device 140. As a result, the rendering processing unit 136 generates a parallax image group. The terminal device 140, for example, acquires a parallax image group from the workstation 130 or the image storage device 120, and displays the parallax image group on the display unit 142. This enables the doctor or the laboratory technician who is the operator of the terminal device 140 to browse the medical image capable of being viewed stereoscopically with the various types of information (e.g., a scale, a patient's name, and an examination item) depicted thereon.

However, even if various nine-parallax images generated by using the same rendering conditions are displayed on the display unit 142, the stereoscopic effect of the stereoscopic image sensed by the operator of the terminal device 140 (observer of the display unit 142) may not always be uniform. FIG. 8A, FIG. 8B, FIG. 8C, and FIG. 8D are schematics for explaining an example of a factor that causes non-uniformity in a stereoscopic effect of a stereoscopic image.

A subject portion in volume data has various shapes three-dimensionally. A subject portion extracted by the segmentation processing unit 1361g illustrated in FIG. 5, for example, has various shapes three-dimensionally.

An assumption is made that, to generate nine-parallax images by the perspective projection method based on "geometric conditions in rendering processing (the parallax number: nine, and the parallactic angle: 1 degree)" set as the rendering conditions, the operator determines a line passing through the center of gravity of a subject portion to be a rotation axis and that the operator moves the viewpoint position along the circumference of a precise circle set on a plane orthogonal to the rotation axis.

Figure 8A:
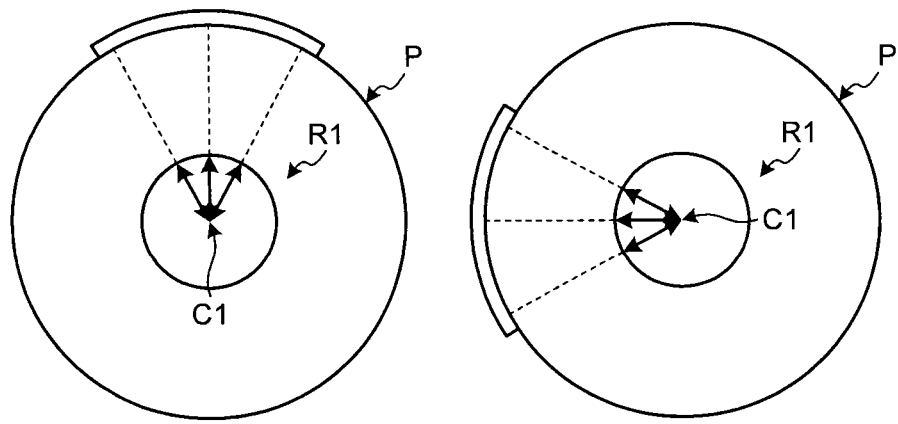
FIG. 8A, FIG. 8B, FIG. 8C, and FIG. 8D are schematics for explaining an example of a factor that causes non-uniformity in a stereoscopic effect of a stereoscopic image.

As illustrated in FIG. 8A, an assumption is made that the shape of an outline of a subject portion R1 cut with a precise circle P along which the viewpoint position is moved is a precise circle. In this case, as illustrated in FIG. 8A, the distance between a center of gravity C1 of the subject portion R1 and the outline of the subject portion R1 is constant even in different viewpoint positions. Therefore, in the case illustrated in FIG. 8A, even if the viewpoint position is located on the upper side of the precise circle P, or even if the viewpoint position is located on the left side of the precise circle P, the observer of the display unit 142 serving as a nine-parallax monitor can observe the nine-parallax images with a uniform stereoscopic effect.

The shape of the subject portion, however, is not always a precise circle. If the shape of the subject portion is not a precise circle, the distance between the center of gravity of the subject portion and the outline of the subject portion changes depending on the viewpoint positions.

Figure 8B:
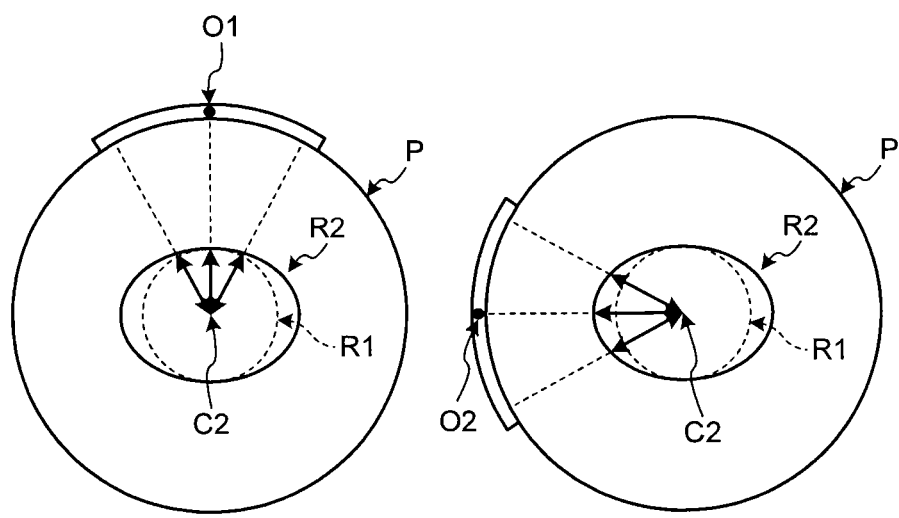

As illustrated in FIG. 8B, for example, an assumption is made that the shape of an outline of a subject portion R2 cut with the precise circle P along which the viewpoint position is moved is an ellipse. Specifically, the ellipse corresponding to the subject portion R2 illustrated in FIG. 8B circumscribes the precise circle corresponding to the subject portion R1 illustrated in FIG. 8A. In this case, as illustrated in FIG. 8B, the distance between a center of gravity C2 and the outline of the subject portion R2 on a line connecting the viewpoint and the center of gravity C2 of the subject portion R2 changes depending on the viewpoint positions. Furthermore, as illustrated in FIG. 8B, the distance between the center of gravity C2 and the outline of the subject portion R2 changes significantly between the case where the viewpoint direction is in a longitudinal direction of the subject portion R2 and the case where the viewpoint direction is in a lateral direction of the subject portion R2.

The case where nine-parallax images of "the parallax number: nine, and the parallactic angle: 1 degree" are generated by using a viewpoint O1 illustrated in FIG. 8B as a reference position and are output to be displayed on the "nine-parallax monitor" is referred to as a first case. By contrast, the case where nine-parallax images of "the parallax number: nine, and the parallactic angle: 1 degree" are generated by using a viewpoint O2 illustrated in FIG. 8B as a reference position and are output to be displayed on the "nine-parallax monitor" is referred to as a second case.

In comparison between the first case and the second case, the distance from the viewpoint located when volume rendering is performed to the outline of the subject portion in the second case is shorter than that in the first case. Furthermore, in comparison between the first case and the second case, the distance from the center of gravity of the subject portion to the outline of the subject portion in the second case is longer than that in the first case. As a result, even if a stereoscopic-vision image generated on the same conditions of "the parallax number: nine, and the parallactic angle: 1 degree" is displayed on the "nine-parallax monitor", a stereoscopic effect (a sense of depth) sensed by the observer is larger in the second case than in the first case. In other words, even if a stereoscopic image is displayed by using nine-parallax images generated on the same rendering conditions, the stereoscopic effect sensed by the observer changes in different viewpoint positions depending on the shape of the subject portion. The factor that causes non-uniformity in the stereoscopic effect of the stereoscopic image described above is based on the premise that the distance between the viewpoint and the center of gravity of the subject portion is constant.

As described above, the shape of the subject portion is a factor that causes non-uniformity in the stereoscopic effect of a stereoscopic image. In addition to the shape of the subject portion, examples of the factor that causes non-uniformity in the stereoscopic effect of a stereoscopic image include a major factor of "protrusion criticality" determined by hardware specifications of the display unit 142 serving as a stereoscopic display monitor. In other words, the non-uniformity in the stereoscopic effect of a stereoscopic image is caused by the relationship between the "distance from the center of gravity of the subject portion to the outline of the subject portion" determined by the shape of the subject portion and the "protrusion criticality" determined by the hardware specifications of the display unit 142 serving as a stereoscopic display monitor. The "protrusion criticality" will be described below.

The stereoscopic effect sensed by the observer who refers to the display unit 142 serving as a stereoscopic display monitor has a limit depending on the specifications of the display unit 142. In other words, the amount capable of being displayed on the display unit 142 in the protruding direction (protruding amount) has a limit (criticality) depending on the specifications of the display unit 142. Hereinafter, a critical value of the protruding amount is referred to as a "protruding critical amount". More specifically, the "protruding critical amount" is a value determined based on a "visual distance, which is a distance between the display surface of the stereoscopic display monitor and the observer who observes the stereoscopic display monitor" and the "hardware specifications of the stereoscopic display monitor". The visual distance between the stereoscopic display monitor and the observer fails to be determined if the position of the observer is not specified. Generally, however, the display unit 142 and the like serving as a stereoscopic display monitor are designed by assuming an observation position from which the stereoscopic display monitor is observed to be a predetermined position. Therefore, the "protruding critical amount" is calculated based on an "assumed visual distance", which is a distance between the observation position assumed to be the predetermined position and the display surface of the stereoscopic display monitor, and on the hardware specifications of the stereoscopic display monitor.

The "protruding critical amount" is a value calculated by Equation (1), for example. In Equation (1), a direction closer to the viewpoint of the observer from the display surface in the depth direction is positive with the origin at the display surface of the stereoscopic display monitor.

$$\text{Protruding Limit Amount(mm)} = \text{Assumed Visual Distance}/\{2 \times [(\text{Assumed Visual Distance} + \text{Gap})/\text{Assumed Visual Distance}] \times (\text{Sub-Pixel Pitch}/\text{Gap}) \times \text{Protruding Limit Frequency} + 1\} \qquad (1)$$

Figure 8C:
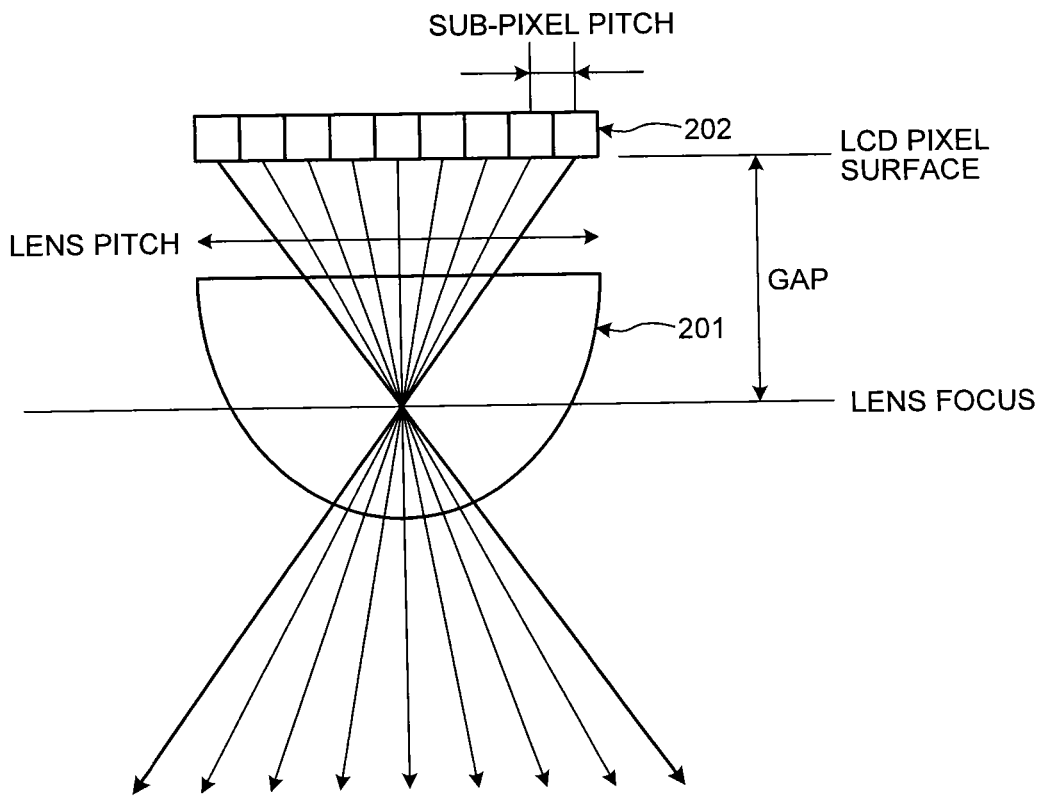

The "gap", the "sub-pixel pitch", and other elements in Equation (1) will now be described with reference to FIG. 8C. FIG. 8C is a schematic of the stereoscopic display monitor exemplified in FIG. 3 viewed in the vertical direction. As illustrated in FIG. 8C, the "gap" represents a distance between a liquid crystal display (LCD) pixel surface and a focus of a lenticular lens (the vertical lenticular sheet 201). The "sub-pixel pitch" represents a distance between LCD pixels (pixels 202) arranged in the stereoscopic display monitor. A "lens pitch" represents the length of a parallax number of LCD pixels (pixels 202) in the lateral direction, and is calculated by "Sub-Pixel Pitch×Parallax Number".

The unit of the "protruding limit frequency" in Equation (1) is "circles per radian (CPR)", and the "protruding limit frequency" is represented by "maximum displayable frequency×N (0<N≤1)". The "maximum displayable frequency" is represented by "Visual Distance/(2×Lens pitch)", and represents the resolution on the display surface of the stereoscopic display monitor. More specifically, the "CPR" represents the density of rays acceptable by a ray cone spreading from the eyes of the observer among the rays emitted from the stereoscopic display monitor. In the same visual distance, the "CPR" increases as the density of arrangement of the lenticular lenses increases, and decreases as the density of arrangement of the lenticular lenses decreases. In other words, in the same density of arrangement of the lenticular lenses, the "CPR" increases as the visual distance increases, and decreases as the visual distance decreases. The "maximum displayable frequency" is the resolution at which the "CPR" is the maximum. In other words, the "maximum displayable frequency" represents the resolution on the display surface of the stereoscopic display monitor.

Figure 8D:
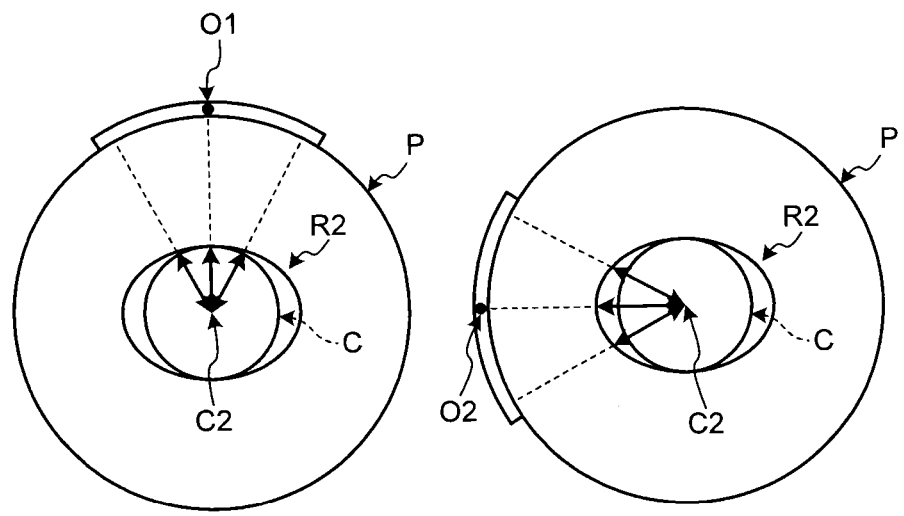

If the "distance from the center of gravity of the subject portion to the outline of the subject portion" exceeds the "protrusion criticality" determined by the "protruding critical amount" calculated by Equation (1), a blur occurs in a stereoscopic image displayed on the stereoscopic display monitor. As illustrated in FIG. 8D, for example, an assumption is made that the outline of the subject portion R2 circumscribes protrusion criticality C. In this case, in a stereoscopic image obtained by generating nine-parallax images based on the viewpoint O1 as the reference position and displaying the nine-parallax images on the "nine-parallax monitor", the "distance from the center of gravity of the subject portion to the outline of the subject portion" is a value close to the "protrusion criticality", whereby a blur is unlikely to occur. By contrast, in a stereoscopic image obtained by generating nine-parallax images based on the viewpoint O2 as the reference position and displaying the nine-parallax images on the "nine-parallax monitor", the "distance from the center of gravity of the subject portion to the outline of the subject portion" exceeds the "protrusion criticality", whereby a blur occurs.

Furthermore, even if the "distance from the center of gravity of the subject portion to the outline of the subject portion" is constant at all angles like the subject portion R1 illustrated in FIG. 8A, for example, a blur occurs at all angles in the stereoscopic image if the distance exceeds the "protrusion criticality".

Therefore, to prevent a blur from occurring in the stereoscopic image, the distance from the center of gravity of the subject portion to the outline of the subject portion is preferably within the protrusion criticality with respect to viewpoints from all angles. In addition, even if the distance from the center of gravity of the subject portion to the outline of the subject portion is within the protrusion criticality, the distance from the viewpoint to the outline of the subject portion may not be constant, and the distance from the center of gravity of the subject portion to the outline of the subject portion may also not be constant with respect to viewpoints from all angles depending on the shape of the subject portion as explained with reference to FIG. 8A and FIG. 8B. As a result, the stereoscopic effect of the stereoscopic image may change depending on the viewpoints.

The protrusion criticality is a value determined by the hardware specifications of the stereoscopic display monitor. The distance from the center of gravity of the subject portion to the outline of the subject portion is a value determined by rendering conditions.

To display a stereoscopic-vision image that provides the optimum stereoscopic effect, the control unit 145 according to the first embodiment, when generating a predetermined parallax number of parallax images from volume data that is three-dimensional medical image data, changes the parallactic angle between the parallax images based on the shape of the subject portion. The control unit 145 then performs control so as to display the predetermined parallax number of parallax images at the changed parallactic angle on the display unit 142. Specifically, the control unit 145 according to the first embodiment changes the parallactic angle between the parallax images based on the relationship between the shape of the subject portion and the protrusion criticality, which is criticality in the protruding direction of the stereoscopic image displayed on the display unit 142.

In the present embodiment, for example, the control unit 145 receives specification of volume data used for generating nine-parallax images and rendering conditions used for generating nine-parallax images from the volume data from the operator via the input unit 141. Subsequently, the control unit 145 changes the parallactic angle set as the rendering conditions depending on the shape of the subject portion determined by the rendering conditions thus received. Subsequently, in the present embodiment, the control unit 145 performs control so as to display nine-parallax images at the changed parallactic angle on the display unit 142.

Specifically, the control unit 145 according to the first embodiment controls the rendering processing unit 136 that performs rendering processing on volume data so as to generate the predetermined parallax number of parallax images at the changed parallactic angle. The control unit 145 according to the first embodiment then performs control so as to display the image group generated by the rendering processing unit 136 on the display unit 142.

In the present embodiment, the control unit 145 replaces the parallactic angle set as the rendering conditions with the changed parallactic angle, thereby resetting the rendering conditions. The control unit 145 then notifies the control unit 135 of the volume data thus specified and the rendering conditions thus reset via the communication unit 143 and the communication unit 133. The control unit 135 acquires the volume data thus specified from the image storage device 120, and controls the rendering processing unit 136 so as to generate nine-parallax images from the volume data thus acquired based on the rendering conditions thus reset. The control unit 135 then stores the nine-parallax images generated by the rendering processing unit 136 in the storage unit 144 of the terminal device 140 via the communication unit 133 and the communication unit 143. The control unit 145 converts the nine-parallax images stored in the storage unit 144 into an intermediate image, and displays the intermediate image on the display unit 142.

Figure 9:
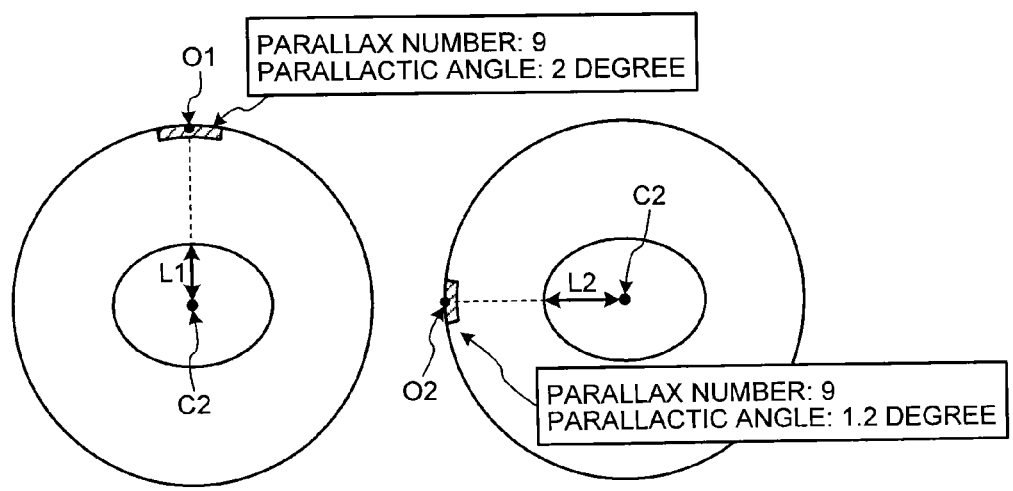
FIG. 9, FIG. 10A, and FIG. 10B are schematics for explaining a specific example of parallactic angle changing processing.
Figure 10A:
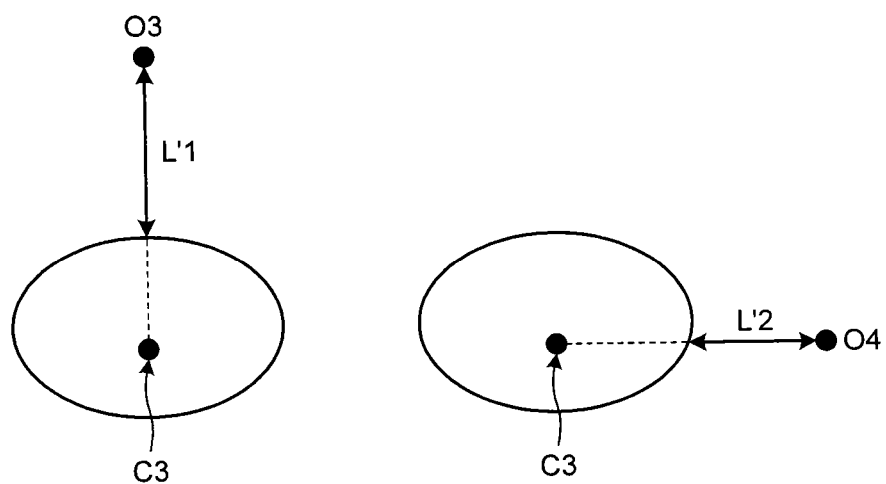
Figure 10B:
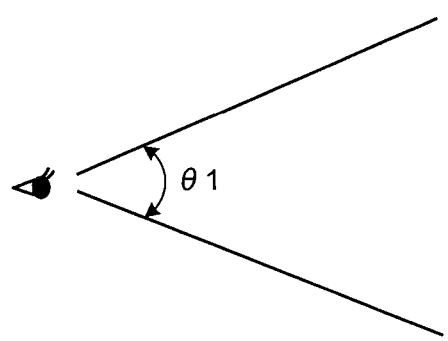

An explanation will be made of a specific example of parallactic angle changing processing performed by the control unit 145 depending on the shape of the subject portion determined by the rendering conditions. FIG. 9, FIG. 10A, and FIG. 10B are schematics for explaining the specific example of the parallactic angle changing processing.

An explanation is made of the case where the distance from the center of gravity of the subject portion to the outline of the subject portion is within the protrusion criticality. The protrusion critical amount of the display unit 142 is stored in the storage unit 144 in advance, for example. In the example illustrated in FIG. 9, the control unit 145 changes the parallactic angle between the parallax images based on the distance from the center of gravity set in the subject portion for moving the viewpoint position as a geometric condition in the rendering processing to the outline of the subject portion. Specifically, the control unit 145 changes the parallactic angle such that the parallactic angle increases as the distance from the center of gravity to the outline decreases. In other words, if the distance from the center of gravity to the outline is small, the control unit 145 makes the parallactic angle large, thereby enhancing the stereoscopic effect.

The control unit 145, for example, uses a function "F(L)" for calculating a parallactic angle at which the stereoscopic effect sensed by the observer is uniform by substituting a distance (L) from the center of gravity to the outline.

The control unit 145 acquires positional information of the outline of the subject portion from positional information of the subject portion extracted by the segmentation processing unit 1361g. Furthermore, the control unit 145 acquires positional information of the center of gravity of the subject portion from the positional information of the subject portion and the voxel value of the subject portion. The control unit 145 acquires positional information on volume data to be processed and the subject portion from the control unit 135.

The control unit 145 then acquires positional information of an intersection of a line extending from a viewpoint serving as a reference to the center of gravity of the subject portion and the outline of the subject portion to calculate the distance from the center of gravity to the outline.

As illustrated in FIG. 9, for example, the control unit 145 acquires positional information of an intersection of a line extending from the viewpoint O1 serving as a reference of nine viewpoints to the center of gravity C2 and the outline of the subject portion to calculate a distance "L1" from the center of gravity to the outline. The control unit 145 then substitutes "L1" into the function "F(L)", thereby deriving "the parallactic angle: 2 degrees" as illustrated in FIG. 9, for example. As a result, the control unit 145 resets rendering conditions for generating nine parallax images of "the parallax number: nine, and the parallactic angle: 2 degrees" with the viewpoint O1 as the reference instead of nine parallax images of "the parallax number: nine, and the parallactic angle: 1 degree" with the viewpoint O1 as the reference.

Furthermore, as illustrated in FIG. 9, the control unit 145 acquires positional information of an intersection of a line extending from the viewpoint O2 serving as a reference of nine viewpoints to the center of gravity C2 and the outline of the subject portion to calculate a distance "L2" from the center of gravity to the outline. The control unit 145 then substitutes "L2" into the function "F(L)", thereby deriving "the parallactic angle: 1.2 degrees" as illustrated in FIG. 9, for example. As a result, the control unit 145 resets rendering conditions for generating nine parallax images of "the parallax number: nine, and the parallactic angle: 1.2 degrees" with the viewpoint O2 as the reference instead of nine parallax images of "the parallax number: nine, and the parallactic angle: 1 degree" with the viewpoint O2 as the reference.

If the distance from the center of gravity of the subject portion to the outline of the subject portion is within the protrusion criticality, performing such processing enables the operator of the terminal device 140 to observe the stereoscopic image with an approximately uniform stereoscopic effect even if the viewpoint position is changed on the trajectory of the precise circle whose center is at the center of gravity, for example. By changing the parallactic angle, the subject portion is partially reduced or enlarged virtually. Therefore, by making the parallactic angle large, the subject portion may possibly exceed the protrusion criticality because of the virtual partial enlargement. To address this, when making the parallactic angle large, the control unit 145 sets an upper limit so as to prevent the subject portion from exceeding the protrusion criticality because of the changed parallactic angle. The control unit 145 calculates the upper limit based on the shape of the subject portion and the protruding critical amount.

An explanation will be made of the case where the distance from the center of gravity of the subject portion to the outline of the subject portion exceeds the protrusion criticality. In this case, the control unit 145 according to the first embodiment makes the parallactic angle set as the rendering conditions small, thereby partially reducing the subject portion virtually such that the outline of the subject portion comes close to the vicinity of the protrusion criticality. Thus, the control unit 145 prevents a blur from occurring in the stereoscopic image.

The control unit 145, for example, uses a table in which "the ratio between the 'distance from the center of gravity of the subject portion to the outline of the subject portion' and the 'protruding critical amount of the display unit 142'" is associated with a "parallactic angle at which the outline of the subject portion comes close to the vicinity of the protrusion criticality" to change the parallactic angle.

By referring to the table, the control unit 145 acquires "the parallactic angle: 1 degree" identical to the rendering condition of "the parallactic angle: 1 degree" as the parallactic angle in the viewpoint O1, for example. Furthermore, by referring to the table, the control unit 145 acquires "the parallactic angle: 0.5 degree" smaller than the rendering condition of "the parallactic angle: 1 degree" as the parallactic angle in the viewpoint O2, for example. As a result, the control unit 145 resets rendering conditions for generating nine parallax images of "the parallax number: nine, and the parallactic angle: 0.5 degree" with the viewpoint O2 as the reference instead of nine parallax images of "the parallax number: nine, and the parallactic angle: 1 degree" with the viewpoint O2 as the reference.

The explanation has been made of the case where, if the subject portion exceeds the protrusion criticality, the control unit 145 makes the parallactic angle small such that the outline of the subject portion comes close to the vicinity of the protrusion criticality, thereby preventing a blur from occurring. Alternatively, if the subject portion is within the protrusion criticality, the control unit 145 according to the present embodiment may make the parallactic angle set as the rendering conditions large by using the table described above, for example. As a result, the control unit 145 can cause the outline of the subject portion to come close to the vicinity of the protrusion criticality, thereby enhancing the stereoscopic effect of the stereoscopic image on a viewpoint from an arbitrary angle at the maximum.

If the viewpoint position is moved on the trajectory of the precise circle whose center is at the center of gravity, processing same as the processing performed in the case of the subject portion being within the protrusion criticality as described above may also be performed even if the subject portion exceeds the protrusion criticality. In other words, the control unit 145 may change the parallactic angle based on the distance from the center of gravity to the outline within a reduction range in which the subject portion is within the protrusion criticality such that the stereoscopic effect of the stereoscopic image on each viewpoint is approximately uniform after the parallactic angle is changed. If "the parallactic angle: 0.5 degree" is set on the viewpoint O2 as described above, for example, the control unit 145 may change the parallactic angle on the viewpoint O1 so as to provide the same stereoscopic effect as that of the stereoscopic image of nine-parallax images on the viewpoint O2.

The control unit 145, for example, uses a function "F' (L$\alpha$, $\theta\alpha$, L$\beta$)" for calculating a parallactic angle ($\theta\beta$) on a view point $\beta$ at which the stereoscopic effect sensed by the observer on a viewpoint $\alpha$ is uniform by substituting "a distance (L$\alpha$) from the center of gravity to the outline on the viewpoint $\alpha$", "a parallactic angle ($\theta\alpha$) on the viewpoint $\alpha$", and "a distance (L$\beta$) from the center of gravity to the outline on the viewpoint $\beta$". The control unit 145 substitutes "L$\alpha$=L2, $\theta\alpha$=0.5, L$\beta$=L1" into the function "F' (L$\alpha$, $\theta\alpha$, L$\beta$)", thereby deriving the parallactic angle on the viewpoint O1. If the subject portion reduced or enlarged virtually by applying the parallactic angle on the viewpoint O1 thus calculated is within the protrusion criticality, the control unit 145 performs parallactic angle changing processing of the viewpoint O1. Performing such processing enables the observer to observe the stereoscopic image without a blur and to observe the stereoscopic image with an approximately uniform stereoscopic effect on a viewpoint from an arbitrary angle.

The explanation has been made of the case where, to display the stereoscopic image with an approximately uniform stereoscopic effect on a viewpoint from an arbitrary angle, the parallactic angle between the parallax images is changed based on the distance from the center of gravity of the subject portion to the outline thereof. The center of gravity of the subject portion is a point set in the subject portion for moving the viewpoint position as a geometric condition of the rendering conditions. In other words, application of the specific example described above is limited to the case where the movement of the viewpoint is rotational movement about the center of gravity.

The factor that causes non-uniformity in the stereoscopic effect of the stereoscopic image in the case of the subject portion being within the protrusion criticality is not limited to the factor illustrated in FIG. 8A and FIG. 8B. Examples of the geometric condition serving as the factor that causes non-uniformity in the stereoscopic effect of the stereoscopic image in the case of the subject portion being within the protrusion criticality include the "viewpoint position", the "direction of the line of sight", and a "viewing angle" set as rendering conditions in the perspective projection method. The viewing angle is an emission angle of light radially emitted from a light source set at the viewpoint.

The control unit 145 changes the parallactic angle between the parallax images based on the distance from the viewpoint to the outline of the subject portion calculated from the viewpoint and the direction of the line of sight set as the geometric conditions. In other words, the control unit 145 changes the parallactic angle depending on the magnitude of the distance from the viewpoint to the outline.

If the subject portion is within the protrusion criticality, for example, the control unit 145 uses a function "F2(L')" for calculating a parallactic angle at which the stereoscopic effect sensed by the observer is uniform by substituting a distance (L') from the viewpoint to the outline.

The control unit 145 acquires positional information of the outline of the subject portion, and calculates the distance from the viewpoint to the outline of the subject portion based on the viewpoint and the direction of the line of sight.

As illustrated in FIG. 10A, an assumption is made that the control unit 145 receives a viewpoint O3 serving as a reference of nine viewpoints as a geometric condition of the rendering conditions, and receives a direction extending from the viewpoint O3 to a point C3 in the subject portion as a direction of the line of sight, for example. In this case, as illustrated in FIG. 10A, the control unit 145 acquires positional information of an intersection of a line extending from the viewpoint O3 to the point C3 and the outline of the subject portion to calculate a distance "L'1" from the viewpoint to the outline.

The control unit 145 then substitutes "L'1" into the function "F2(L')", thereby deriving a changed parallactic angle. As a result, the control unit 145 resets rendering conditions for generating nine parallax images of "the parallax number: nine, and the parallactic angle: 2 degrees" with the viewpoint O3 as the reference.

Furthermore, as illustrated in FIG. 10A, an assumption is made that the control unit 145 receives a viewpoint O4 serving as a reference of nine viewpoints as a geometric condition of the rendering conditions, and receives a direction extending from the viewpoint O4 to the point C3 as a direction of the line of sight, for example. In this case, as illustrated in FIG. 10A, the control unit 145 acquires positional information of an intersection of a line extending from the viewpoint O4 to the point C3 and the outline of the subject portion to calculate a distance "L'2" from the viewpoint to the outline.

The control unit 145 then substitutes "L'2" into the function "F2(L')", thereby deriving a changed parallactic angle. As a result, the control unit 145 resets rendering conditions for generating nine parallax images of "the parallax number: nine, and the parallactic angle: 1.2 degrees" with the viewpoint O4 as the reference.

If the subject portion is within the protrusion criticality, performing such processing enables the operator of the terminal device 140 to observe the stereoscopic image with an approximately uniform stereoscopic effect even if the viewpoint position and the direction of the line of sight are changed arbitrarily, for example.

By contrast, if the subject portion exceeds the protrusion criticality, the control unit 145 may perform the following processing. Specifically, the control unit 145 performs parallactic angle changing processing for causing the outline of the subject portion to come close to the vicinity of the protrusion criticality. Subsequently, the control unit 145 changes the parallactic angle based on the distance from the viewpoint to the outline within a reduction range in which the subject portion is within the protrusion criticality such that the stereoscopic effect of the stereoscopic image on each viewpoint is approximately uniform after the parallactic angle is changed.

As described above, examples of the geometric condition serving as the factor that causes non-uniformity in the stereoscopic effect of the stereoscopic image in the case of the subject portion being within the protrusion criticality include the "viewing angle". Therefore, the control unit 145 changes the parallactic angle between the parallax images based on the viewing angle set as the geometric conditions. In other words, the control unit 145 changes the parallactic angle between the parallax images depending on the magnitude of the viewing angle.

The control unit 145, for example, uses a function "F3(θ)" for calculating a parallactic angle at which the stereoscopic effect sensed by the observer is uniform by substituting a viewing angle (θ).

As illustrated in FIG. 10B, for example, the control unit 145 receives a viewing angle "θ1" from nine viewpoints as a geometric condition of the rendering conditions. In this case, as illustrated in FIG. 10B, the control unit 145 substitutes "θ1" into the function "F3(θ)", thereby deriving a changed parallactic angle. As a result, the control unit 145 resets rendering conditions.

Performing such processing enables the operator of the terminal device 140 to observe the stereoscopic image with an approximately uniform stereoscopic effect even if the viewing angle is changed arbitrarily, for example. The subject portion included in the viewing angle changes depending on the shape of the subject portion and the viewpoint position. To address this, the control unit 145 changes the parallactic angle depending on the size of the subject portion included in the viewing angle set as the geometric condition.

If the subject portion exceeds the protrusion criticality, the control unit 145 may perform the following processing. Specifically, the control unit 145 performs parallactic angle changing processing for causing the outline of the subject portion to come close to the vicinity of the protrusion criticality. Subsequently, the control unit 145 changes the parallactic angle based on the viewing angle within a reduction range in which the subject portion is within the protrusion criticality such that the stereoscopic effect of the stereoscopic image on each viewpoint is approximately uniform after the parallactic angle is changed.

Furthermore, it is known that the optimum parallactic angle differs depending on appearance conditions, such as a color, in the rendering processing. Therefore, in the parallactic angle changing processing described above, the parallactic angle may be changed depending on appearance conditions in the rendering processing. The storage unit 144, for example, stores therein a table in which a color set as an appearance condition is associated with the optimum parallactic angle. The control unit 145 refers to the table to perform the parallactic angle changing processing. Furthermore, instead of using the function "F(L)", the function "F2(L')", and the function "F3(θ)", the control unit 145 may refer to a table in which the distance "L" is associated with the optimum parallactic angle, a table in which the distance "L'" is associated with the optimum parallactic angle, and a table in which the viewing angle "θ" is associated with the optimum parallactic angle to perform the parallactic angle changing processing.

If the subject portion exceeds the protrusion criticality, the control unit 145 may perform the following processing. Specifically, the control unit 145 performs parallactic angle changing processing for causing the outline of the subject portion to come close to the vicinity of the protrusion criticality. Subsequently, the control unit 145 changes the parallactic angle based on the appearance conditions within a reduction range in which the subject portion is within the protrusion criticality such that the stereoscopic effect of the stereoscopic image on each viewpoint is approximately uniform after the parallactic angle is changed.

As described above, the control unit 145 according to the first embodiment changes the parallactic angle between the parallax images based on at least one of the geometric conditions and the appearance conditions set as the rendering conditions.

The processing performed by the image processing system 1 according to the first embodiment will now be described with reference to FIG. 11. FIG. 11 is a flowchart for explaining the processing performed by the terminal device included in the image processing system according to the first embodiment.

As illustrated in FIG. 11, the control unit 145 of the terminal device 140 included in the image processing system 1 according to the first embodiment determines whether rendering conditions for volume data specified as a target to be processed are received (Step S101). If no rendering condition is received (No at Step S101), the control unit 145 waits until rendering conditions are received.

By contrast, if rendering conditions are received (Yes at Step S101), the control unit 145 changes a parallactic angle specified by the rendering conditions based on the relationship between the shape of the subject portion set as the rendering conditions and the protrusion criticality (Step S102). The control unit 145 then resets rendering conditions with the changed parallactic angle (Step S103), and notifies the workstation 130 of the rendering conditions thus reset (Step S104). By the control of the control unit 135 to which the rendering conditions thus reset are notified, the rendering processing unit 136 generates nine-parallax images.

The control unit 145 then determines whether the communication unit 143 receives the nine-parallax images from the workstation 130 (Step S105). If the nine-parallax images are not received (No at Step S105), the control unit 145 waits until the nine-parallax images are received.

By contrast, if the nine-parallax images are received (Yes at Step S105), the control unit 145 converts the nine-parallax images thus received into an intermediate image, and outputs the intermediate image to the display unit 142. Subsequently, the display unit 142 displays the nine-parallax images (Step S106), and the processing is terminated.

As described above, in the first embodiment, the parallactic angle between the parallax images is changed based on the shape of the subject portion. Specifically, in the first embodiment, the parallactic angle between the parallax images is changed based on the relationship between the shape of the subject portion and the protrusion criticality. As a result, the observer of the display unit 142 serving as a nine-parallax monitor can observe a clear stereoscopic image using nine-parallax images even if the rendering conditions are changed with various patterns. Furthermore, the observer of the display unit 142 serving as a nine-parallax monitor can observe the stereoscopic image using nine-parallax images with an approximately uniform stereoscopic effect even if the rendering conditions are changed with various patterns. Therefore, according to the first embodiment, it is possible to display a stereoscopic-vision image that provides the optimum stereoscopic effect.

Second Embodiment

In a second embodiment, an explanation will be made of the case where an image group that meets rendering conditions obtained after changing the parallactic angle is selected.

A control unit 145 according to the second embodiment selects an image group composed of a predetermined parallax number of parallax images at the changed parallactic angle from an image group generated in advance by a rendering processing unit 136 that performs rendering processing on volume data. The control unit 145 then performs control such that a display unit 142 displays the image group thus selected.

Figure 12A:
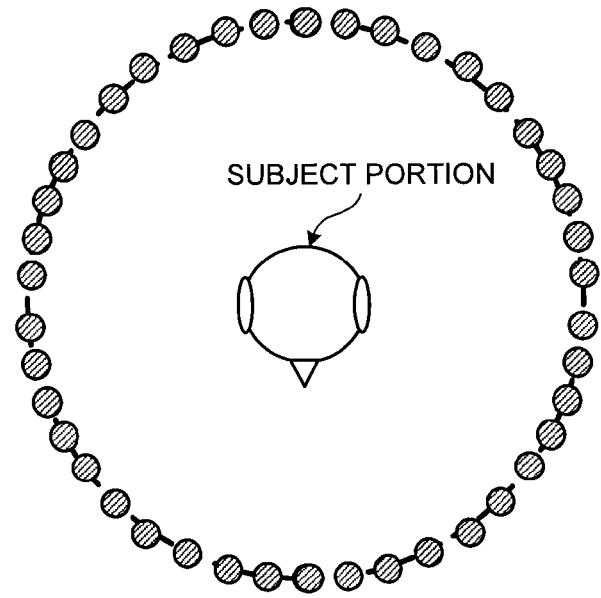
FIG. 12A, FIG. 12B, and FIG. 12C are schematics for explaining a parallax image group generated in advance by a rendering processing unit according to a second embodiment.
Figure 12B:
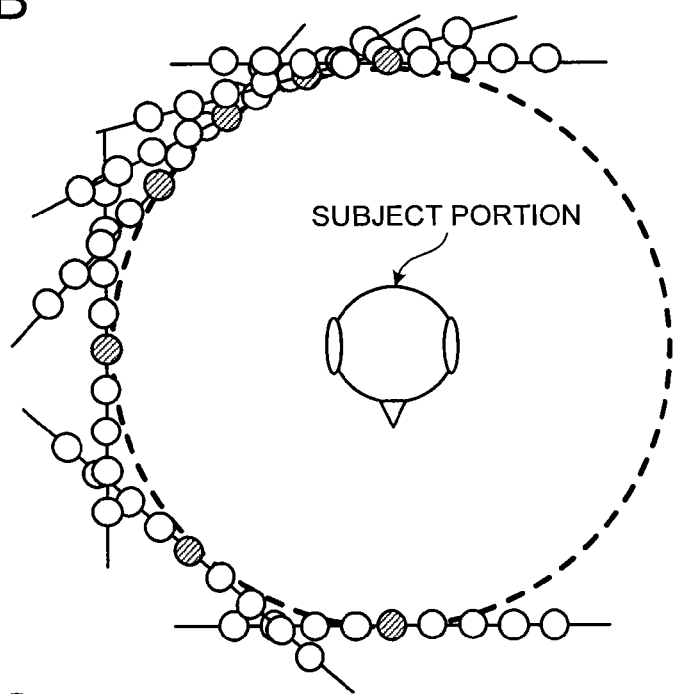
Figure 12C:
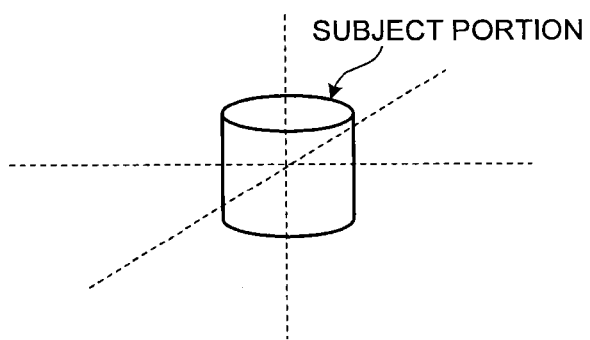

To perform such control processing, a control unit 135 according to the second embodiment instructs the rendering processing unit 136 to generate a parallax image group in advance based on various rendering conditions from volume data stored in an image storage device 120. FIG. 12A, FIG. 12B, and FIG. 12C are schematics for explaining the parallax image group generated in advance by the rendering processing unit according to the second embodiment.

To make it possible to change the parallactic angle between parallax images arbitrarily in accordance with the changed parallactic angle, for example, the control unit 135 sets a precise circle on a section passing through the center of gravity of a subject portion as illustrated in FIG. 12A. The control unit 135 then sets 360 viewpoints along the entire circumference of the precise circle such that the parallactic angle is 1 degree. In FIG. 12A, while 42 viewpoints alone are depicted for convenience of illustration, 360 viewpoints are actually set. The rendering processing unit 136 uses the 360 viewpoints thus set to generate a parallax image group composed of 360 parallax images. As illustrated in FIG. 12A, the parallax images on the entire circumference generated for a rendering target are hereinafter referred to as entire circumference data.

The control unit 135 may set a plurality of precise circles on the same plane by setting a plurality of radii of the precise circles. The control unit 135 may generate entire circumference data composed of 720 parallax images by setting "the parallactic angle: 0.5 degree", for example. The control unit 135 may generate the entire circumference data by setting an arbitrary point in the subject portion instead of the center of gravity of the subject portion, and setting a plurality of viewpoints on a precise circle whose center is at the point thus set. The figure on which the viewpoints for generating the entire circumference data are set is not limited to a precise circle, and may be a figure in an arbitrary shape, such as an ellipse and a polygon.

Alternatively, the control unit 135 may generate the entire circumference data by the following method. Specifically, to make it possible to change the parallactic angle between parallax images arbitrarily in accordance with the changed parallactic angle, the control unit 135 sets a plurality of reference viewpoints (refer to shaded circles in FIG. 12B) on the precise circle as illustrated in FIG. 12B. The control unit 135 then sets nine viewpoints along a tangent passing through each of the reference viewpoints thus set such that the parallactic angle is 1 degree. The rendering processing unit 136 uses the nine viewpoints set on each tangent to generate nine-parallax images for each reference viewpoint by the parallel projection method explained in FIG. 6A.

The interval between the reference viewpoints set in the entire circumference data illustrated in FIG. 12B is set to 1 degree or 0.5 degree. Similarly to the example described above, the control unit 135 may set a plurality of precise circles on the same plane by setting a plurality of radii of the precise circles. The control unit 135 may generate the entire circumference data illustrated in FIG. 12B by setting an arbitrary point in the subject portion instead of the center of gravity of the subject portion, and setting a plurality of reference viewpoints on a precise circle whose center is at the point thus set. The figure on which the reference viewpoints for generating the entire circumference data illustrated in FIG.

12B are set is not limited to a precise circle, and may be a figure in an arbitrary shape, such as an ellipse and a polygon.

As illustrated in FIG. 12C, the control unit 135 sets a plurality of rotation axes passing through a point in the subject portion (e.g., the center of gravity). Thus, the control unit 135 sets an arbitrary shaped figure on a section obtained by cutting the subject portion in an arbitrary direction, and performs control such that the entire circumference data illustrated in FIG. 12A and FIG. 12B is generated in each figure.

The control unit 135 then stores the parallax image group generated by the rendering processing unit 136 in a storage unit 134 or the image storage device 120 in a manner associated with the volume data serving as a generation source. An explanation will be made of the case where the parallax image group is stored in the image storage device 120 via the communication unit 133.

The operator of the terminal device 140 inputs specification of volume data and rendering conditions via an input unit 141 in the same manner as in the first embodiment. The control unit 145 then acquires a parallax image group associated with the volume data received by the input unit 141 from the image storage device 120. Specifically, the control unit 145 controls a communication unit 143 so as to transmit additional information of the volume data input by the operator to the image storage device 120. The image storage device 120 then retrieves the volume data associated with the additional information thus received, and transmits an image group associated with the volume data thus retrieved to the terminal device 140.

Figure 13A:
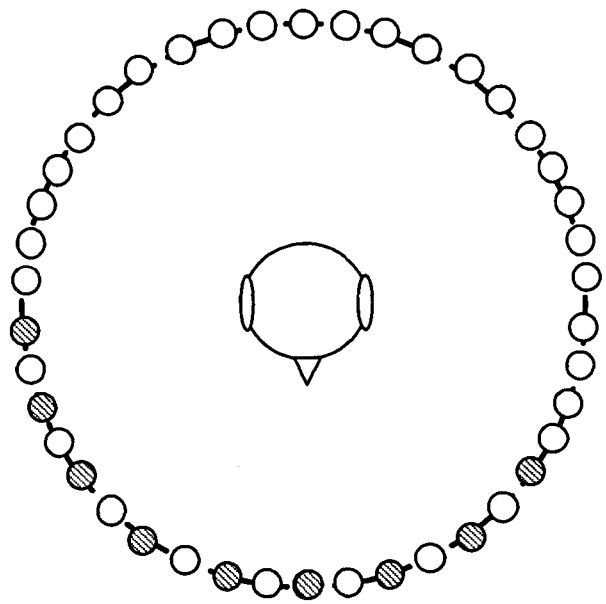
FIG. 13A and FIG. 13B are schematics for explaining a control unit according to the second embodiment.
Figure 13B:
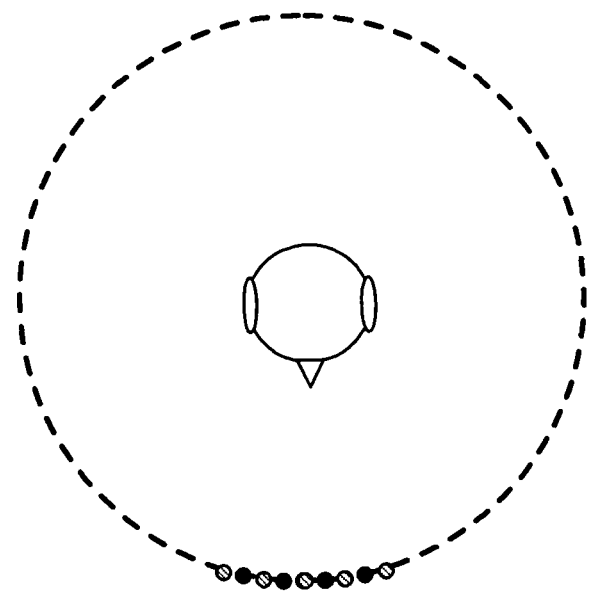

The control unit 145 selects an image group composed of a predetermined parallax number of parallax images (nine-parallax images) at a changed parallactic angle from parallax image groups received by the communication unit 143. The control unit 145 then converts the image group thus selected into an intermediate image, and displays the intermediate image on the display unit 142. FIG. 13A and FIG. 13B are schematics for explaining the control unit according to the second embodiment.

An assumption is made that entire circumference data of "the parallactic angle: 1 degree" is received as a parallax image group and that the changed parallactic angle is "the parallactic angle: 2 degrees", for example. In this case, the control unit 145 determines that a parallax image group of "the parallactic angle: 2 degrees" can be selected from the entire circumference data of "the parallactic angle: 1 degree". Subsequently, as illustrated in FIG. 13A, the control unit 145 selects nine parallax images alternately from the entire circumference data of "the parallactic angle: 1 degree" so as to achieve "the parallactic angle: 2 degrees". The control unit 145 then displays the nine images thus selected on the display unit 142.

The control unit 145 according to the second embodiment may perform control so as to generate a predetermined parallax number of parallax images at a changed parallactic angle by interpolation processing using an image group generated in advance by the rendering processing unit 136, and to display the image group thus generated on the display unit 142.

Specifically, the control unit 145 uses an interpolation function of a two-dimensional image processing unit 146. As described above, the two-dimensional image processing unit 146 has an interpolation function to use depth information of each of two parallax images and to generate a new parallax image from the two parallax images by interpolation processing.

A specific example of the interpolation processing performed by the two-dimensional image processing unit 146 will now be described. To generate an image C located in the middle of an image A and an image B, for example, the two-dimensional image processing unit 146 derives a "warp field between the image A and the image B" indicating a direction from the image A to the image B by a "mutual information method". The two-dimensional image processing unit 146 then adds an intermediate point of each pixel vector in the "warp field" (half the vector from the image A to the image B) to the image A, thereby generating the image C. If not an image located in the middle of the image A and the image B, but an image C at an angular position of "2:1" is required, for example, the two-dimensional image processing unit 146 uses a pixel of a vector from the image A to the image B located in the ratio of "2:1" to generate the image C. If the angular interval between the image A and the image B is small, the two-dimensional image processing unit 146 may perform simple interpolation processing for adding the image A and image B and dividing the pixel value of the added image into halves, for example, without using the depth information.

Such interpolation processing is performed when the parallax image groups received by the communication unit 143 include no nine-parallax images at the changed parallactic angle, for example. An assumption is made that entire circumference data of "the parallactic angle: 1 degree" is received as a parallax image group and that a changed parallactic angle is "the parallactic angle: 0.5 degrees", for example. In this case, the control unit 145 determines that all the nine-parallax images of "the parallactic angle: 0.5 degrees" fail to be selected from the entire circumference data of "the parallactic angle: 1 degree". Subsequently, the control unit 145 controls the two-dimensional image processing unit 146 so as to generate a parallax image at a viewpoint position represented by a filled circle in FIG. 13B from acquired two adjacent parallax images by interpolation processing. In other words, the two-dimensional image processing unit 146 uses depth information of each of the two parallax images generated from two viewpoints adjacent to the viewpoint position represented by the filled circle, and generates a new parallax image corresponding to the viewpoint position represented by the filled circle by interpolation processing. Thus, the control unit 145 causes the display unit 142 to output nine parallax images of "the parallactic angle: 0.5 degrees".

The processing performed by an image processing system 1 according to the second embodiment will now be described with reference to FIG. 14. FIG. 14 is a flowchart for explaining the processing performed by the terminal device included in the image processing system according to the second embodiment.

As illustrated in FIG. 14, the terminal device 140 of the image processing system 1 according to the second embodiment determines whether volume data as a target to be processed is specified and rendering conditions for the volume data are received (Step S201). If no volume data is specified and no rendering condition is received from the operator (No at Step S201), the terminal device 140 is in a standby mode.

By contrast, if volume data is specified and rendering conditions are received from the operator (Yes at Step S201), the control unit 145 acquires a parallax image group associated with the volume data thus specified (Step S202).

The control unit 145 then changes a parallactic angle specified by the rendering conditions based on the relationship between the shape of the subject portion set as the rendering conditions and the protrusion criticality (Step S203). Subsequently, the control unit 145 acquires nine-parallax images at the changed parallactic angle by selection processing or interpolation processing (Step S204).

The control unit 145 then converts the nine-parallax images thus acquired into an intermediate image, and outputs the intermediate image to the display unit 142. Subsequently, the display unit 142 displays the nine-parallax images (Step S205), and the processing is terminated.

As described above, in the second embodiment, a predetermined parallax number of parallax images at a changed parallactic angle can be displayed on the display unit 142 without generating the parallax images in real time. In other words, in the second embodiment, a predetermined parallax number of parallax images at a changed parallactic angle can be displayed without performing volume rendering processing. Therefore, according to the second embodiment, it is possible to promptly display a stereoscopic-vision image that provides the optimum stereoscopic effect.

In the embodiments, while the explanation has been made of the case where a nine-parallax monitor is used, the parallactic angle changing processing explained in the embodiments can be applied to the case where a two-parallax monitor is used. Furthermore, in the embodiments, the explanation has been made of the case where the control unit 145 of the terminal device 140 performs the parallactic angle changing processing. However, the embodiments are not limited thereto, and the control unit 135 of the workstation 130 may perform the parallactic angle changing processing, for example. In this case, the control unit 135 requests the control unit 145 to display the nine-parallax images at the changed parallactic angle on the display unit 142.

In the embodiments, the apparatus that performs the rendering processing may be the medical image diagnosis apparatus 110. In the embodiments, for example, the medical image diagnosis apparatus 110 may perform the rendering processing, and the workstation 130 and the terminal device 140 may perform the parallactic angle changing processing.

The "parallactic angle changing processing and display of the parallax image group at the changed parallactic angle" explained in the embodiments may be performed only by the medical image diagnosis apparatus 110, only by the workstation 130, or only by the terminal device 140.

In other words, the processing explained in the embodiments can be realized by distributing and integrating the processing functionally or physically in arbitrary units in accordance with various types of loads and usage of the devices included in the image processing system 1. Furthermore, all or an arbitrary part of the processing functions performed in the devices can be realized by a CPU or a computer program analyzed and executed by the CPU, or can be realized as hardware using wired logic.

The image processing method explained in the embodiments can be realized by executing an image processing program prepared in advance by a computer, such as a personal computer and a workstation. The image processing program may be distributed via a network such as the Internet. Furthermore, the image processing program may be recorded in a computer-readable recording medium, such as a hard disk, a flexible disk (FD), a compact disk read-only memory (CD-ROM), a magneto-optical disk (MO), a digital versatile disk (DVD), and a Blu-ray Disc (registered trademark), and may be executed by being read from the recording medium by the computer.

As described above, according to the first and the second embodiments, it is possible to display a stereoscopic-vision image that provides the optimum stereoscopic effect.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An image processing system comprising:
a stereoscopic display device configured to display a stereoscopic image viewed by an observer stereoscopically by displaying a predetermined parallax number of parallax images; and
circuitry configured to, when generating the predetermined parallax number of parallax images from volume data that is three-dimensional medical image data on which a subject is depicted, perform control so as to change a parallactic angle between parallax images as a condition of rendering processing on the volume data for generating the parallax images on which the subject is depicted based on a shape of the subject portion according to a viewpoint position as the condition of the rendering processing and to display a predetermined parallax number of parallax images generated by the parallactic angle thus changed on the stereoscopic display device.

2. The image processing system according to claim 1, wherein the circuitry is configured to change the parallactic angle between the parallax images based on a relationship between the shape of the subject portion and protrusion criticality that is criticality in a protruding direction of the stereoscopic image displayed on the stereoscopic display device.

3. The image processing system according to claim 1, wherein the circuitry is configured to change the parallactic angle between the parallax images based on at least one of a geometric condition and an appearance condition set as a rendering condition for the subject portion.

4. The image processing system according to claim 3, wherein the circuitry is configured to change the parallactic angle between the parallax images based on a distance from the center of gravity set in the subject portion for moving a viewpoint position as the geometric condition to an outline of the subject portion.

5. The image processing system according to claim 3, wherein the circuitry is configured to change the parallactic angle between the parallax images based on a distance from a viewpoint to an outline of the subject portion calculated from the viewpoint and a direction of a line of sight, the viewpoint and the direction of a line of sight being set as the geometric condition.

6. The image processing system according to claim 3, wherein the circuitry is configured to change the parallactic angle between the parallax images based on a viewing angle set as the geometric condition.

7. The image processing system according to claim 1, wherein the circuitry is configured to control a rendering processor that performs rendering processing on the volume data so as to generate the predetermined parallax number of parallax images at the changed parallactic angle, and is configured to perform control such that an image group generated by the rendering processor is displayed on the stereoscopic display device.

8. The image processing system according to claim 1, wherein the circuitry is configured to perform control such that an image group composed of the predetermined parallax number of parallax images at the changed parallactic angle is selected from an image group generated in advance by a rendering processor that performs rendering processing on the volume data and such that the image group thus selected is displayed on the stereoscopic display device.

9. The image processing system according to claim 8, wherein the circuitry is configured to perform control such that the predetermined parallax number of parallax images at the changed parallactic angle is generated by interpolation processing using the image group generated in advance by the rendering processor that performs rendering processing on the volume data and such that an image group thus generated is displayed on the stereoscopic display device.

10. An image processing method comprising, when generating a predetermined parallax number of parallax images from volume data that is three-dimensional medical image data on which a subject is depicted, performing control, by circuitry, so as to change a parallactic angle between parallax images as a condition of rendering processing on the volume data for generating the parallax images on which the subject is depicted based on a shape of the subject portion according to a viewpoint position as the condition of the rendering processing and to display a predetermined parallax number of parallax images generated by the parallactic angle thus changed on a stereoscopic display device.

* * * * *